(12) United States Patent
Aoki

(10) Patent No.: US 10,822,329 B2
(45) Date of Patent: *Nov. 3, 2020

(54) METHOD FOR PRODUCING GLYCERIC ACID ESTER

(71) Applicant: KAO CORPORATION, Tokyo (JP)

(72) Inventor: Takashi Aoki, Wakayama (JP)

(73) Assignee: KAO CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/473,167

(22) PCT Filed: Dec. 26, 2017

(86) PCT No.: PCT/JP2017/046814
§ 371 (c)(1),
(2) Date: Jun. 24, 2019

(87) PCT Pub. No.: WO2018/124148
PCT Pub. Date: Jul. 5, 2018

(65) Prior Publication Data
US 2020/0087290 A1    Mar. 19, 2020

(30) Foreign Application Priority Data

Dec. 27, 2016 (JP) ................. 2016-253829
Dec. 27, 2016 (JP) ................. 2016-253833
Dec. 27, 2016 (JP) ................. 2016-253836
Dec. 27, 2016 (JP) ................. 2016-253843

(51) Int. Cl.
| | |
|---|---|
| *C07D 407/12* | (2006.01) |
| *C07B 61/00* | (2006.01) |
| *C07C 45/65* | (2006.01) |
| *C07C 213/00* | (2006.01) |
| *C07D 317/32* | (2006.01) |
| *C07D 319/06* | (2006.01) |
| *C07B 41/12* | (2006.01) |
| *C07C 49/17* | (2006.01) |
| *C07C 215/10* | (2006.01) |

(52) U.S. Cl.
CPC ............ *C07D 407/12* (2013.01); *C07B 61/00* (2013.01); *C07C 45/65* (2013.01); *C07C 213/00* (2013.01); *C07D 317/32* (2013.01); *C07D 319/06* (2013.01); *C07B 41/12* (2013.01); *C07C 49/17* (2013.01); *C07C 215/10* (2013.01)

(58) Field of Classification Search
CPC ........................... C07D 407/12; C07D 317/12
USPC .................................................. 549/448, 453
See application file for complete search history.

(56) References Cited

U.S. PATENT DOCUMENTS

| | | |
|---|---|---|
| 5,821,374 A | 10/1998 | Jenny et al. |
| 7,851,639 B2 | 12/2010 | Hayat et al. |
| 2007/0197790 A1 | 8/2007 | Belgsir et al. |
| 2012/0014889 A1 | 1/2012 | Miller et al. |

FOREIGN PATENT DOCUMENTS

| | | |
|---|---|---|
| CN | 1939904 A | 4/2007 |
| CN | 101412706 A | 4/2009 |
| DE | 3900479 A1 | 7/1990 |

(Continued)

OTHER PUBLICATIONS

Badalyan et al., "Cooperative Electrocatalytic Alcohol Oxidation with Electron-Proton-Transfer Mediators", Nature, vol. 535, No. 7612, 2016, pp. 406-410.

(Continued)

*Primary Examiner* — Charanjit Aulakh
(74) *Attorney, Agent, or Firm* — Element IP, PLC

(57) ABSTRACT

The present invention relates to providing a novel glyceric acid ester which can be produced in a high yield and is expected to be applied as a synthetic intermediate, and a method of producing the same. In addition, the present invention relates to providing a novel glyceric acid ester which exhibits a high recovery in a water-washing step after the reaction and a small work load at the time of production, and is expected to be applied as a synthetic intermediate, and a method of producing the same. The present invention provides a method of producing a compound represented by the following formula (II), including a step of oxidatively esterifying a compound represented by the following formula (I):

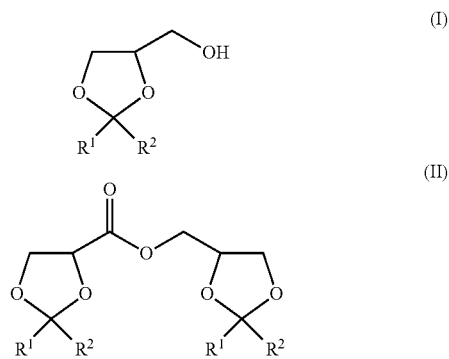

wherein, in the formulae (I) and (II), $R^1$ and $R^2$ each independently represent a hydrogen atom or a monovalent hydrocarbon group, or $R^1$ and $R^2$ are bonded to each other to form a divalent hydrocarbon group for constituting a ring structure, provided that the case where $R^1$ and $R^2$ are a methyl group at the same time is excluded.

15 Claims, 4 Drawing Sheets

(56) References Cited

FOREIGN PATENT DOCUMENTS

| EP | 1669353 A1 | 6/2006 |
|---|---|---|
| JP | 2006-219406 A | 8/2006 |
| WO | WO 2012/041845 A1 | 4/2012 |
| WO | WO 2014/140017 A1 | 9/2014 |
| WO | WO-2015181747 A1 | 12/2015 |
| WO | WO 2016/097840 A1 | 6/2016 |

OTHER PUBLICATIONS

De Luca et al., "Trichloroisocyanuric/TEMPO Oxidation of Alcohols under Mild Conditions: A Close Investigation", Journal of Organic Chemistry, vol. 68, No. 12, 2003, pp. 4999-5001.

English translation of Decision to Grant a Patent for Japanese Patent Application No. 2017-250263, dated Aug. 24, 2018.

English translation of Decision to Grant a Patent for Japanese Patent Application No. 2017-250264, dated Aug. 15, 2018.

English translation of Decision to Grant a Patent for Japanese Patent Application No. 2017-250267, dated Aug. 24, 2018.

English translation of Descision to Grant a Patent for Japanese Application No. 2017-250262, dated Aug. 28, 2018.

English translation of Notice of Reasons for Refusal for Japanese Patent Application No. 2017-250262, dated Jun. 18, 2018.

English translation of Notice of Reasons for Refusal for Japanese Patent Application No. 2017-250263, dated Jun. 4, 2018.

English translation of Notice of Reasons for Refusal for Japanese Patent Application No. 2017-250264, dated Jun. 4, 2018.

English translation of Notice of Reasons for Refusal for Japanese Patent Application No. 2017-250267, dated Jun. 4, 2018.

Ermolenko et al., "An Expedient One-Step Preparation of (S)-2,3-O-Isopropylidene-glyceraldehyde", Synlett, vol. 10, 2001, pp. 1565-1566.

Hamlin et al., "Dehydrogenation of Perfluoroalkyl Ketones by Using a Recyclable Oxoammonium Salt", European Journal of Organic Chemistry, vol. 18, 2013, pp. 3658-3661.

Herath et al., 2,2,6,6-Tetramethyl piperidine-1-oxyl (TEMPO)-mediated catalytic oxidation of benzyl alcohol in acetonitrile and ionic liquid 1-butyl-3-methyl-imidazolium hexafluorophosphate [BMim][$PF_6$]: Kinetic analysis, Electrochimica Acta, vol. 53, No. 12, 2008, pp. 4324-4330.

Hon et al., "Tishchenko Reactions and Oppenauer Oxidation Reactions of Aldehydes Promoted by Diisobutylaluminum Hydride", Tetrahedron Letters, vol. 45, No. 16, 2004, pp. 3313-3315.

Hon et al., "Tishchenko Reactions of Aldehydes Promoted by Diisobutylaluminum Hydride and its Application of the Macrocyclic Lactone Formation", Tetrahedron, vol. 63, No. 46, 2007, pp. 11325-11340.

International Search Report for International Application No. PCT/JP2017/046814 dated Feb. 6, 2018.

Kataky et al., "Chiral Resolution of R and S 1-Phenylethanol on Glassy Carbon Electrodes", Journal of Electroanalytical Chemistry, vol. 633, No. 1, 2009, pp. 57-62.

Li et al., "α-Aminoxylation of Ketones and β-Chloro-α-aminoxylation of Enones with TEMPO and Chlorocatecholborane", Organic Letters, vol. 14, No. 17, 2012, pp. 4474-4477.

Merbouh et al., "Oxoammonium Salts. 9. Oxidative Dimerization of Polyfunctional Primary Alcohols to Esters. An Interesting β Oxygen Effect", Journal of Organic Chemistry, vol. 69, No. 15, 2004, pp. 5116-5119.

Shibuya et al., "2-Azaadamantane N-Oxyl (AZADO and I-Me-AZADO: High Efficient Organocatalysts for Oxidation of Alcohols", Journal of the American Chemical Society, vol. 128, No. 26, 2006, pp. 8412-8413.

Sorbye et al., Preparation of Protected Serinol, Synthetic Communications, vol. 27, No. 16, 1997, pp. 2813-2816.

Wang et al., "Domino Radical Addition/Oxidation Sequence with Photocatalysis: One-Pot Synthesis of Polysubstituted Furans from α-Chloro-Alkyl Ketones and Styrenes", Chemistry A European Journal, vol. 22, No. 39, Aug. 19, 2016, pp. 13794-13798.

Wang et al., "The indirect conversion of glycerol into 1,3-dihydroxyacetone over magnetic polystyrene immobilized TEMPO catalyst", Chemical Engineering Journal, vol. 229, 2013, pp. 234-238.

Zheng et al. "Novel Process for 1,3-Dihydroxyacetone Production from Glycerol. 1. Technological Feasibility Study and Process Design" Industrial & Engineering Chemistry Research, vol. 51, 2012, pp. 3715-3721.

Animati et al., "Synthesis and Biological Evaluation of Rebeccamycin Analogues Modified at the Imide Moiety,", Bioorganic & Medicinal Chemistry Letters, vol. 22, 2012 (Available online Jun. 15, 2012), pp. 5013-5017.

Bobbitt et al., "Oxoammonium Salt Oxidations of Alcohols in the Presence of Pyridine Bases," J. Org. Chem., vol. 79, No. 3, 2014 (Date of Publication Jan. 6, 2014), pp. S1-S56 (57 total pages).

Cao et al., "Aerobic Oxidation Catalysis with Stable Radicals," Chem. Commun, vol. 50, 2014 (Published on Mar. 12, 2014), pp. 4524-4543.

Indian Office Action, dated Oct. 1, 2019, for Indian Application No. 201917000304, with an English translation.

Indian Office Action, dated Oct. 11, 2019, for Indian Application No. 201917000294, with an English translation.

Indian Office Action, dated Oct. 4, 2019, for Indian Application No. 201917000301, with an English translation.

Okada et al., "Sodium Hypochlorite Pentahydrate (NaOCl•$5H_2O$) Crystals as an Extraordinary Oxidant for Primary and Secondary Alcohols," Synlett, vol. 25, No. 4, 2014, pp. 596-598 (5 total pages).

U.S. Office Action for U.S. Appl. No. 16/473,177, dated Sep. 5, 2019.

Waidmann et al., "Using combinations of oxidants and bases as PCET reactants: thermochemical and practical considerations," Energy Environ. Sci., vol. 5, Feb. 21, 2012, pp. 7771-7780.

Adi Abramovich et al, "Organocatalytic Oxidative Dimerization of Alcohols to Esters", Synlett, vol. 23, No. 15, 2012, pp. 2261-2265.

Barry M. Trost et al, "Palladium-Catalyzed Trimethylenemethane Reaction to Form Methylenetetrahydrofurans. Aldehyde and Ketone Substrates and the Tin Effect", J. Am. Chem. Soc., vol. III, 1989, pp. 5902-5915.

Extended European Search Report dated Jul. 14, 2020 in Patent Application No. 17888167.8, 9 pages.

International Search Report dated Feb. 6, 2018 in PCT/JP2017/046815 (with English translation), 7 pages.

International Search Report dated Mar. 20, 2018 in PCT/JP2017/046813 (with English translation), 5 pages.

Marek Majewski et al, "1,3-Dioxan-5-ones: synthesis, deprotonation, and reactions of their lithium enolates", Canadian Journal of Chemistry, vol. 73, No. 10, 1995, pp. 1616-1626.

Per H. J. Carlsen et al, "Synthesis of Benzylidene-Protected Dihydroxyacetone", Acta Chemica Scandinavica, vol. 50, 1996, pp. 185-187.

Elina Sproge et al, "Selective liquid phase oxidation of glycerol to glyceric acid over novel supported Pt catalysts", Journal of the Serbian Chemical Society, 78 (9), XP055180440, 2013, pp. 1359-1372.

Extended European Search Report dated Aug. 17, 2020 in Application No. 17885459.2, 6 pages.

U.S. Appl. No. 16/473,065, filed Jun. 24, 2019, U.S. Patent Application Publication No. 2019-0330173 A1, Takashia Aoki.

U.S. Appl. No. 16/473,177, filed Jun. 24, 2019, U.S. Patent Publication No. 2019-0322654 A1, Takashi Aoki.

[Fig. 1]
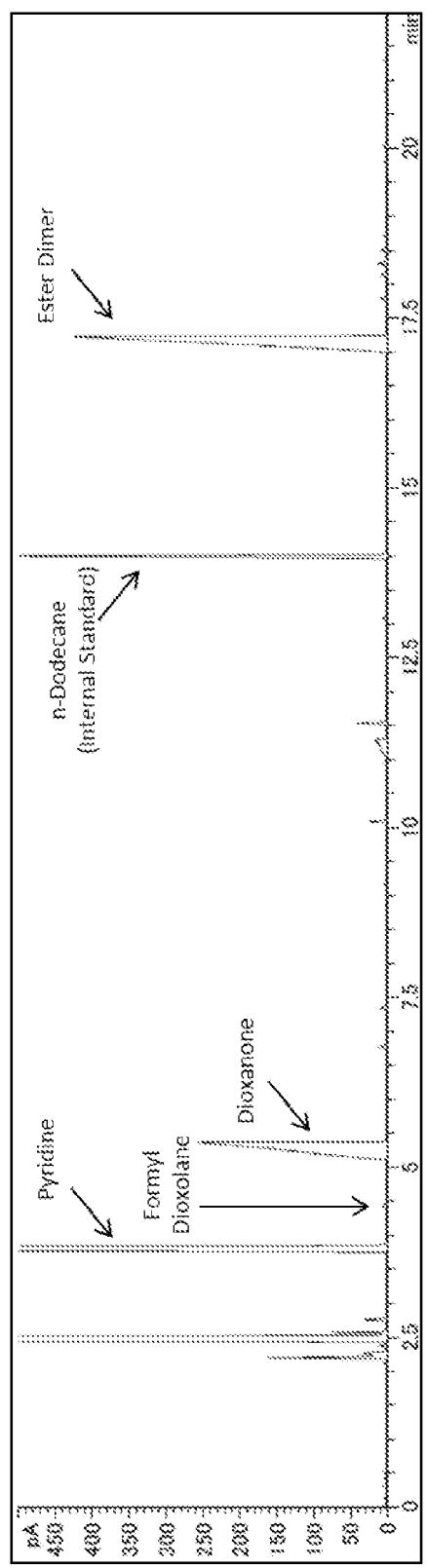

[Fig. 2]
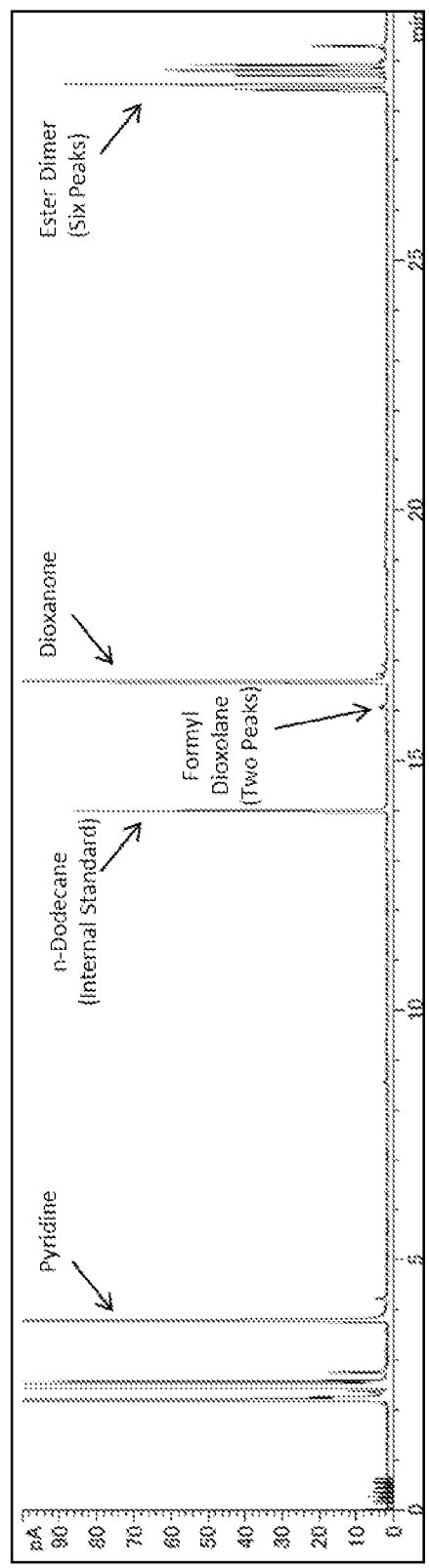

[Fig. 3]
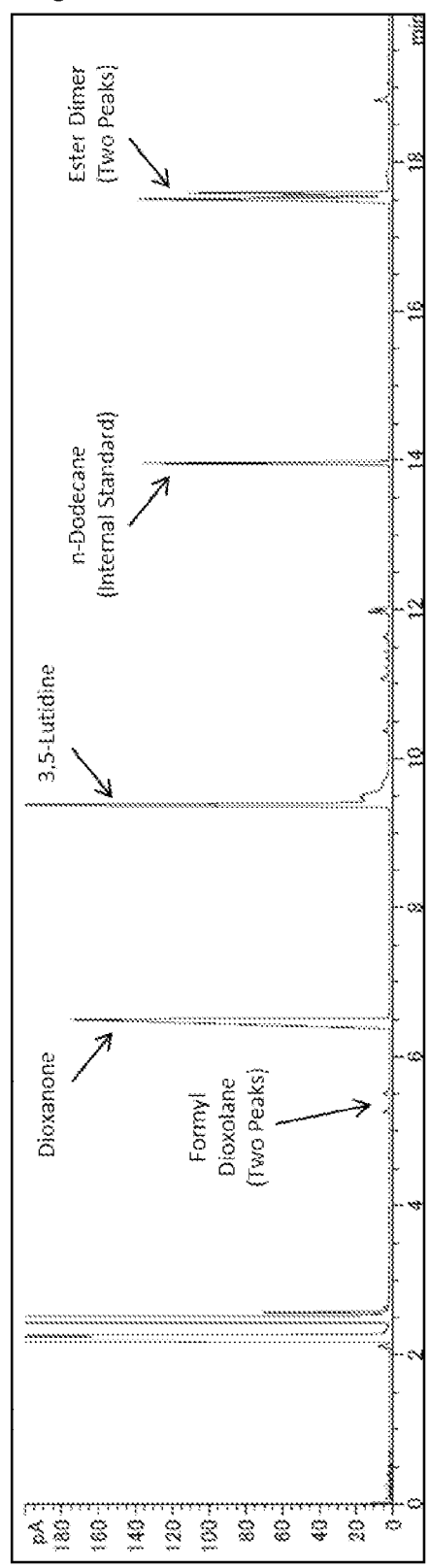

[Fig. 4]
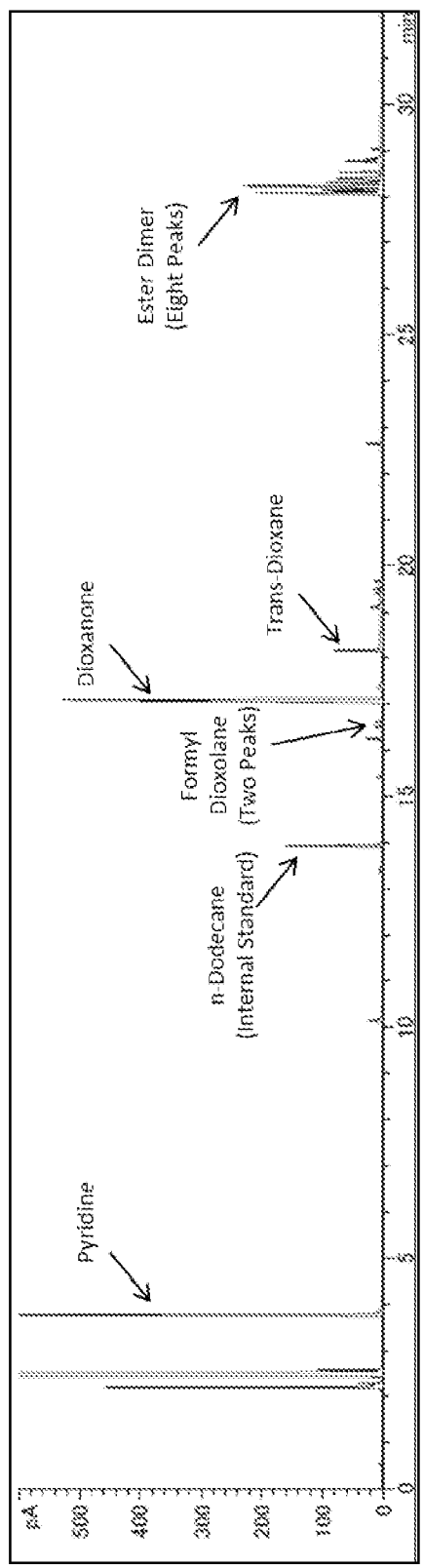

METHOD FOR PRODUCING GLYCERIC ACID ESTER

FIELD OF THE INVENTION

The present invention relates to a method of producing a glyceric acid ester.

BACKGROUND OF THE INVENTION

Compounds having a glyceric acid skeleton in which hydroxy groups at the 2-position and 3-position are protected as a cyclic acetal group are useful as a synthetic intermediate for glyceric acid and an ester thereof having applications as raw materials, for example, for various medicaments, cosmetics, detergents, polymers, or the like.

As for examples of the compounds having a glyceric acid skeleton in which hydroxy groups at the 2-position and 3-position are protected as a cyclic acetal group, for example, Synlett, Vol. 10, pp. 1565-1566, 2001 (NPL 1), The Journal of Organic Chemistry, Vol. 69, pp. 5116-5119, 2004 (NPL 2), Tetrahedron, Vol. 63, pp. 11325-11340, 2007 (NPL 3), and Synlett, Vol. 23, pp. 2261-2265, 2012 (NPL 4) describe production examples of (2,2-dimethyl-1,3-dioxolan-4-yl)methyl 2,2-dimethyl-1,3-dioxolane-4-carboxylate through a dimerization reaction of 4-hydroxymethyl-2,2-dimethyl-1,3-dioxolane that is producible from glycerol and acetone, or an oxidant thereof, 4-formyl-2,2-dimethyl-1,3-dioxolane.

SUMMARY OF THE INVENTION

The present invention relates to a method of producing a compound represented by the following formula (II), including a step of oxidatively esterifying a compound represented by the following formula (I):

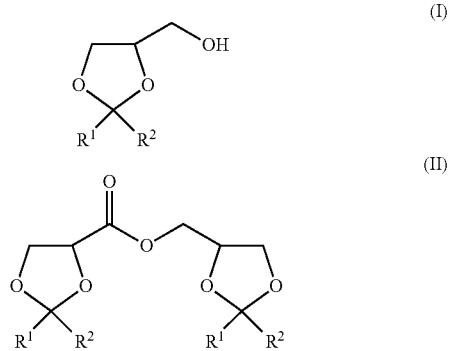

wherein, in the formulae (I) and (II), $R^1$ and $R^2$ each independently represent a hydrogen atom or a monovalent hydrocarbon group, or $R^1$ and $R^2$ are bonded to each other to form a divalent hydrocarbon group for constituting a ring structure, provided that the case where $R^1$ and $R^2$ are a methyl group at the same time is excluded.

Furthermore, the present invention relates to a compound represented by the following formula (II):

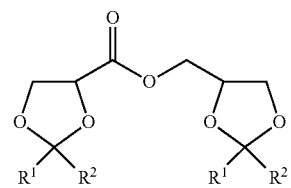

wherein, in the formula (II), $R^1$ and $R^2$ each independently represent a hydrogen atom or a monovalent hydrocarbon group, or $R^1$ and $R^2$ are bonded to each other to form a divalent hydrocarbon group for constituting a ring structure, provided that the case where $R^1$ and $R^2$ are a methyl group at the same time is excluded.

BRIEF DESCRIPTION OF THE DRAWINGS

FIG. 1 is a GC chart of a reaction solution obtained in Example 2-1-1.

FIG. 2 is a GC chart of a reaction solution obtained in Example 2-2-1.

FIG. 3 is a GC chart of a reaction solution obtained in Example 2-3-3.

FIG. 4 is a GC chart of a reaction solution obtained in Example 2-4.

COMPOUND REPRESENTED BY FORMULA (II)

The compound represented by the following formula (II) of the present invention is a novel glyceric acid ester (hereinafter also referred to as "glyceric acid ester of the present invention" or "ester dimer of the present invention").

Glyceric acid and an ester thereof can be produced from the glyceric acid ester of the present invention. In addition, as for the glyceric acid ester of the present invention, in the case where $R^1$ is a hydrogen atom, the compound can be produced in a high yield, and furthermore, in each of steps of from the production to utilization as an intermediate, not only acetalization quickly proceeds, but also stability of an acetal group is high. In the case where $R^1$ and $R^2$ are each a monovalent hydrocarbon group or $R^1$ and $R^2$ are bonded to each other to form a divalent hydrocarbon group for constituting a ring structure, there is also revealed an excellent effect such that the recovery in a water-washing step after the reaction is high, and a work load at the time of production is small.

The methods of producing (2,2-dimethyl-1,3-dioxolan-4-yl)methyl 2,2-dimethyl-1,3-dioxolane-4-carboxylate as described in NPLs 1 to 4 are as follows.

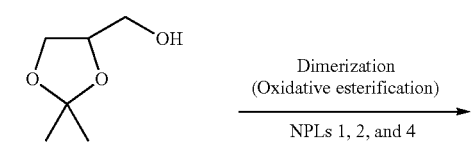

4-Hydroxymethyl-
2,2-dimethyl-1,3-dioxolane

Dimerization
(Oxidative esterification)

NPLs 1, 2, and 4

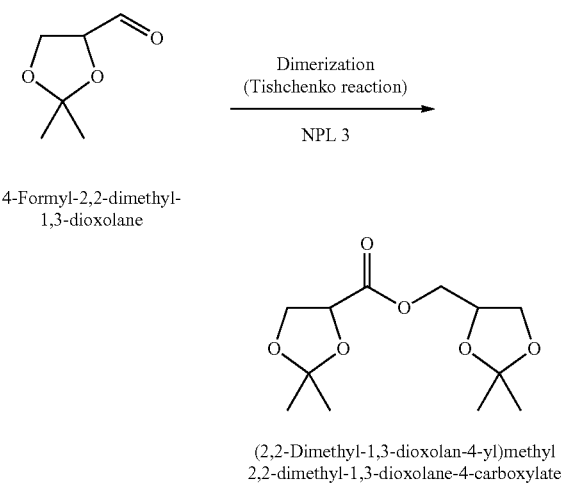

4-Formyl-2,2-dimethyl-
1,3-dioxolane

Dimerization
(Tishchenko reaction)

NPL 3

(2,2-Dimethyl-1,3-dioxolan-4-yl)methyl
2,2-dimethyl-1,3-dioxolane-4-carboxylate

However, the compound having a glyceric acid skeleton in which hydroxy groups at the 2-position and 3-position are protected as a cyclic acetal group as described in NPLs 1 to 4 is only the compound originated from acetone as described above. In addition, this compound was not one which is obtainable in a thoroughly high yield.

In addition, NPLs 1 to 4 are a literature describing the development of a novel dimerization reaction method or a dimer compound obtained as a by-product, but do not provide any description regarding selection of a substrate or reaction conditions for realizing the industrialization of production of a compound having a glyceric acid skeleton in which hydroxy groups at the 2-position and 3-position are protected as a cyclic acetal group or subsequent development of derivatives.

In various reactions using an organic solvent, for the purpose of efficiently removing a catalyst or a by-product, such as an inorganic salt derived from an auxiliary raw material, a step of water-washing an organic layer is generally performed. Meanwhile, when water-solubility of the desired compound is high, the yield is lowered in the water-washing step, resulting in an economic disadvantage, or a work load for recovering the desired compound from an aqueous phase becomes large.

The present invention relates to a novel glyceric acid ester which can be produced in a high yield and is expected to be applied as a synthetic intermediate, and a method of producing the same. In addition, the present invention relates to a novel glyceric acid ester which exhibits a high recovery in a water-washing step after the reaction and a small work load at the time of production and is expected to be applied as a synthetic intermediate, and a method of producing the same.

In accordance with the present invention, a novel glyceric acid ester which can be produced in a high yield and is expected to be applied as a synthetic intermediate, and a method of producing the same can be provided. In addition, in accordance with the present invention, a novel glyceric acid ester which exhibits a high recovery in a water-washing step after the reaction, and a small work load at the time of production and is expected to be applied as a synthetic intermediate, and a method of producing the same can be provided.

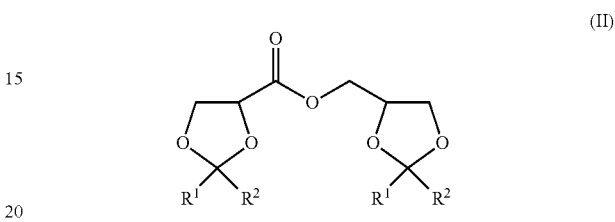

(II)

In the formula (II), $R^1$ and $R^2$ each independently represent a hydrogen atom or a monovalent hydrocarbon group, or $R^1$ and $R^2$ are bonded to each other to form a divalent hydrocarbon group for constituting a ring structure, provided that the case where $R^1$ and $R^2$ are a methyl group at the same time is excluded.

In the formula (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

As a preferred embodiment of $R^1$ and $R^2$, from the viewpoints of availability and reactivity of raw material, stability of the dioxolane or the ester dimer of the present invention, and easiness of recovery of a ketone by-produced through acetal decomposition of the ester dimer of the present invention, preferably, $R^1$ and $R^2$ are each a monovalent hydrocarbon group having 1 or more and 8 or less carbon atoms; more preferably, $R^1$ is a monovalent hydrocarbon group having 1 or more and 8 or less carbon atoms, and $R^2$ is a monovalent hydrocarbon group having 2 or more and 8 or less carbon atoms; still more preferably, $R^1$ is an alkyl group having 1 or more and 8 or less carbon atoms, and $R^2$ is an alkyl group having 2 or more and 8 or less carbon atoms; yet still more preferably, $R^1$ is an alkyl group having 1 or 2 carbon atoms, and $R^2$ is an alkyl group having 2 or more and 6 or less carbon atoms; even yet still more preferably, $R^1$ is an alkyl group having 1 or 2 carbon atoms, and $R^2$ is an alkyl group having 2 or more and 4 or less carbon atoms; and even still more preferably, $R^1$ is a methyl group, and $R^2$ is an ethyl group.

As another preferred embodiment of $R^1$ and $R^2$, $R^1$ and $R^2$ are bonded to each other to form a divalent hydrocarbon group for constituting a ring structure. From the above-mentioned viewpoints, $R^1$ and $R^2$ are preferably bonded to each other to form a divalent hydrocarbon group having 2 or more and 7 or less carbon atoms, more preferably a divalent hydrocarbon group having 3 or more and 6 or less carbon atoms, still more preferably a divalent hydrocarbon group having 4 or more and 5 or less carbon atoms, and yet still more preferably a divalent hydrocarbon group having 5 carbon atoms. That is, the ring structure containing $R^1$ and $R^2$ is preferably a 3- to 8-membered ring, more preferably a 4- to 7-membered ring, still more preferably a 5- to 6-membered ring, and yet still more preferably a 6-membered ring. The ring structure containing $R^1$ and $R^2$ is preferably a cycloalkane structure, more preferably a ring structure having 5 or 6 carbon atoms (cyclopentane ring or cyclohexane ring), and still more preferably a cyclohexane ring.

In the formula (II), in the case where $R^1$ and $R^2$ are bonded to each other to constitute a ring structure, the formula (II) becomes the following formula (II').

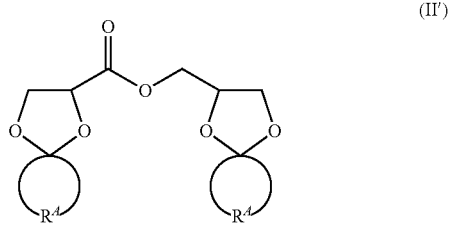 [SMILES: O=C(OCC1COCO1)C1COCO1 ; "RA" ; "RA"]

(II')

In the formula (II'), $R^4$s each indicate a divalent hydrocarbon group to form a ring structure.

In the formula (II'), the ring structure containing $R^A$ is preferably a 3- to 8-membered ring, more preferably a 4- to 7-membered ring, still more preferably a 5- to 6-membered ring, and yet still more preferably a 6-membered ring. The ring structure containing $R^A$ is preferably a cycloalkane structure, and as mentioned above, it is preferred that a cyclopentane ring or a cyclohexane ring is formed, and it is more preferred that a cyclohexane ring is formed.

That is, $R^A$ is preferably an ethylene group (—$(CH_2)_2$—), a trimethylene group (—$(CH_2)_3$—), a tetramethylene group ((—$(CH_2)_4$—), a pentamethylene group (—$(CH_2)_5$—), a hexamethylene group (—$(CH_2)_6$—), or a heptamethylene group (—$(CH_2)_7$—), more preferably a trimethylene group, a tetramethylene group, a pentamethylene group, or a hexamethylene group, still more preferably a tetramethylene group or a pentamethylene group, and yet still more preferably a pentamethylene group.

As a still another preferred embodiment of $R^1$ and $R^2$, in the formula (II), $R^2$ is a hydrogen atom, and $R^1$ represents a hydrogen atom or a monovalent hydrocarbon group. From the viewpoints of availability and reactivity of the aldehyde raw material, stability of the dioxolane or the ester dimer of the present invention, and easiness of recovery of an aldehyde by-produced through acetal decomposition of the ester dimer of the present invention, $R^1$ is preferably a hydrogen atom or a hydrocarbon group having 1 or more and 20 or less carbon atoms. The hydrocarbon group is preferably an alkyl group or an aryl group. The carbon number of the alkyl group is preferably 1 or more, and it is preferably 20 or less, more preferably 18 or less, still more preferably 16 or less, yet still more preferably 14 or less, yet still more preferably 12 or less, yet still more preferably 10 or less, yet still more preferably 8 or less, yet still more preferably 6 or less, yet still more preferably 4 or less, and yet still more preferably 2 or less. Such an alkyl group may be either linear or branched. In addition, the carbon number of the aryl group is preferably 6 or more, and it is preferably 20 or less, more preferably 18 or less, still more preferably 16 or less, yet still more preferably 14 or less, yet still more preferably 12 or less, yet still more preferably 10 or less, yet still more preferably 8 or less, and yet still more preferably 6 or less.

From the aforementioned viewpoints, $R^1$ is preferably a hydrogen atom or a monovalent hydrocarbon group having 1 or more and 20 or less carbon atoms, more preferably a hydrogen atom or a linear alkyl group having 1 or more and 8 or less carbon atoms, a branched alkyl group having 1 or more and 8 or less carbon atoms, or an aryl group having a carbon umber of 6 or more and 20 or less carbon atoms, still more preferably a hydrogen atom, a methyl group, or a phenyl group, and yet still more preferably a hydrogen atom.

In the compound represented by the formula (II), two or more asymmetric carbons are existent. Accordingly, in the case where the asymmetric carbon number is n, stereoisomer mixtures of $2^n$ (2 to the power of n) will exist. In the present invention, the compound represented by the formula (II) may be a stereoisomer mixture and is not particularly limited.

<Production Method of Compound Represented by Formula (II)>

The method of producing the ester dimer of the present invention is not particularly limited, and it is preferred to produce the ester dimer through an oxidative esterification reaction of a compound represented by the following formula (I) (hereinafter also referred to as "dioxolane").

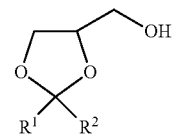

(I)

In the formula (I), $R^1$ and $R^2$ each independently represent a hydrogen atom or a monovalent hydrocarbon group, or $R^1$ and $R^2$ are bonded to each other to form a divalent hydrocarbon group for constituting a ring structure, provided that the case where $R^1$ and $R^2$ are a methyl group at the same time is excluded.

In the present invention, as the dioxolane, the compound presented by the formula (I) may be used alone, or a mixture of the compound represented by the formula (I) and a compound represented by the formula (V) as mentioned later (hereinafter also referred to as "dioxane") may be used. As the mixture of the compound represented by the formula (I) and the compound represented by the formula (V), a product which is marketed as the mixture may be used, or as mentioned later, a mixture of the compound represented by the formula (I) and the compound represented by the formula (V) may be produced and used, and there is no particular limitation. However, from the viewpoint of inexpensive production, it is preferred that a mixture of the dioxolane and the dioxane is produced (synthesized) and used.

<Production of Dioxolane>

The method of producing the dioxolane (the compound represented by the formula (I)), which is used in the present invention, is not limited, and from the viewpoints of availability of raw material, yield, and easiness of reaction operation, the compound is preferably produced by a method of acetalizing glycerol, and a compound represented by the following formula (III) or a multimer thereof in the presence of an acid catalyst (method 1), or a method of subjecting glycerol and a compound represented by the following formula (IV) to acetal exchange in the presence of an acid catalyst (method 2), both of which are generally widely known.

That is, it is preferred that the production method of a glyceric acid ester of the present invention includes the following step 1 and step 2.

Step 1: A step of acetalizing glycerol and a compound represented by the following formula (III) or a multimer thereof in the presence of an acid catalyst (step 1-1), or a step of subjecting glycerol and a compound represented by the following formula (IV) to acetal exchange in the presence of an acid catalyst (step 1-2)

Step 2: A step of oxidatively esterifying a mixture of a compound represented by the following formula (I) and a compound represented by the following formula (V)

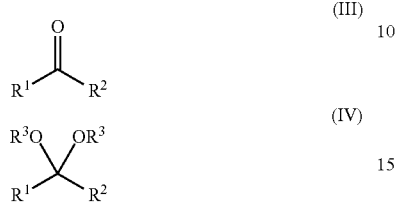

In the formulae (III) and (IV), $R^1$ and $R^2$ are synonymous with $R^1$ and $R^2$ in the formula (II), and $R^3$'s each independently represent a monovalent hydrocarbon group.

In the formula (IV), $R^3$'s each independently represent a monovalent hydrocarbon group, from the viewpoint of availability of raw material, $R^3$ is preferably a hydrocarbon group having 1 or more and 8 or less carbon atoms, and from the viewpoint of promoting a reaction by distilling an alcohol by-produced by the acetal exchange reaction outside the reaction system, $R^3$ is more preferably a monovalent hydrocarbon group having 1 or more and 3 or less carbon atoms, still more preferably a monovalent alkyl group having 1 or more and 3 or less carbon atoms, and yet still more preferably a methyl group.

In the formula (III), in the case where $R^1$ or $R^2$ is a hydrogen atom, examples of the multimer of the compound represented by the formula (III) include paraformaldehyde that is a multimer of formaldehyde and paraldehyde (another name: 2,4,6-trimethyl-1,3,5-trioxane) that is a cyclic trimer of acetaldehyde. Taking into consideration easiness of handling, etc., the compound represented by the formula (III) or a multimer thereof may be properly chosen and used.

In general, the dioxolane obtained by the aforementioned acetalization or acetal exchange method is obtained as a mixture containing a compound represented by the following formula (V) (dioxane) as expressed by the following reaction formula. The isomer ratio of the dioxolane and the dioxane to be used in the present invention is not limited, and from the viewpoints of productivity and economy, it is preferred that the isomer ratio of the dioxolane is high as far as possible.

In the formula (III), in the case where at least one of $R^1$ and $R^2$ is a hydrogen atom, the isomer ratio of the dioxolane is preferably 40% or more and 60% or less.

In the formula (III), in the case where $R^1$ and $R^2$ are each a monovalent hydrocarbon group, the dioxolane obtained from the compound represented by the formula (III) and the compound represented by the formula (IV) is obtained in an isomerization ratio of 95% or more.

<Method 1, Step 1-1>

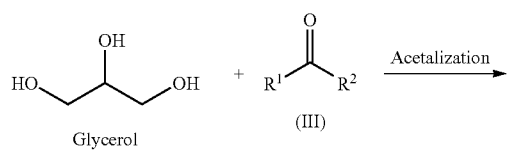

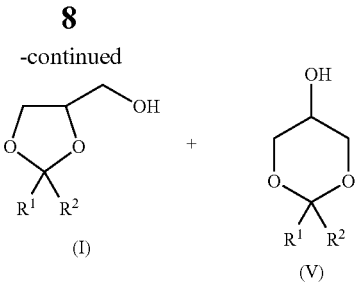

<Method 2, Step 1-2>

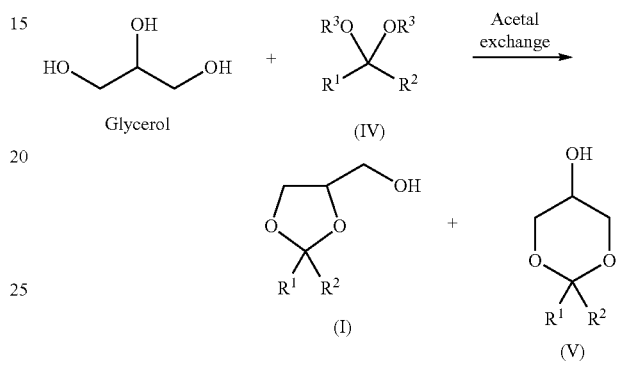

The mixture of the dioxolane (compound represented by the formula (I)) and the dioxane (compound represented by the formula (V)) obtained in the aforementioned method 1 (step 1-1) or method 2 (step 1-2) can be used as it is, or after being purified, as the raw material in the subsequent step, and from the viewpoint of the yield in the subsequent step, it is preferred that the mixture is purified to remove an unreacted raw material, etc., and from the viewpoint of easiness of purification, it is more preferred to perform distillation purification.

In view of the matter that it is difficult to separate the dioxolane and the dioxane from each other through purification, it is preferred to use the dioxolane and the dioxane in a state of mixture as the raw material for the subsequent step.

[Oxidative Esterification]

The glyceric acid ester of the present invention is obtained through oxidative esterification of the aforementioned dioxolane (compound represented by the formula (I)).

The oxidative esterification is one kind of oxidation reaction for obtaining an ester from a primary alcohol and an alcohol in a broad sense and is more generally a reaction for obtaining one molecule of an ester dimer from two molecules of the same primary alcohol, and also has another name, such as oxidative dimerization. In the present invention, the oxidative esterification means that a reaction of obtaining the ester dimer of the present invention (compound represented by the formula (II)) from the dioxolane (compound represented by the formula (I)) is performed.

Examples of the method of oxidative esterification include a method of using a homogeneous or heterogeneous metal catalyst; a method of using 4-acetamido-2,2,6,6-tetramethyl-1-oxopiperidium tetrafluoroborate and pyridine, as described in NPL 1; and a method of using a catalytic amount of 2,2,6,6-tetramethylpiperidine-1-oxyl (hereinafter also referred to as "TEMPO"), an oxidizing agent, and pyridine, as described in NPL 4.

When the mixture of the dioxolane (compound represented by the formula (I)) and the dioxane (compound represented by the formula (V)) is oxidatively esterified, the following reaction occurs representatively.

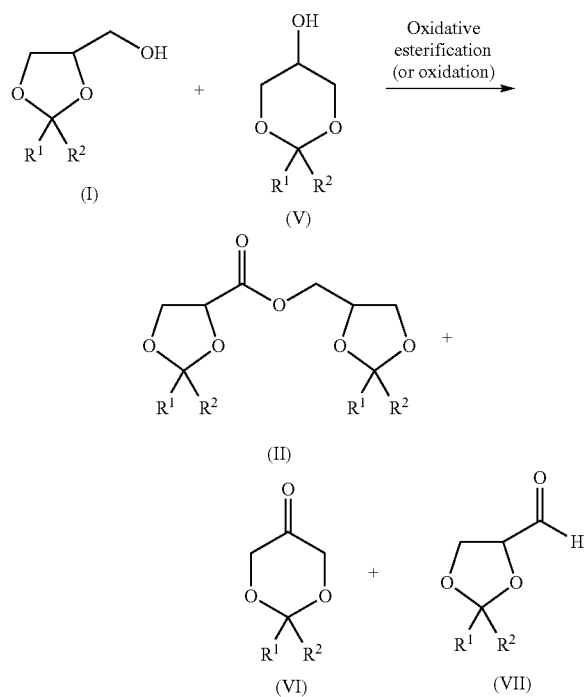

In the formula, $R^1$ and $R^2$ are the same as mentioned above.

As mentioned above, the dioxolane to be used in the present invention is typically a mixture containing the dioxane, and in the oxidative esterification step, a formyl dioxolane (compound represented by the formula (VII)) may be occasionally by-produced depending upon the reaction conditions. The by-production quantity of the formyl dioxolane is not limited, and from the viewpoint of obtaining the ester dimer of the present invention in a high yield, the yield of the formyl dioxolane produced from the dioxolane is preferably 20% or less, more preferably 10% or less, still more preferably 5% or less, yet still more preferably substantially 0%, and even yet still more preferably 0%. In order to decrease the by-production quantity of the formyl dioxolane, a preferred production method as mentioned later may be adopted.

Similarly, in the step of oxidatively esterifying the mixture of the dioxolane and the dioxane, there is a possibility depending upon the reaction conditions that the dioxane does not react, a compound represented by the formula (VI) (hereinafter also referred to as "dioxanone") is produced from the dioxane, or a compound other than the dioxanone is produced, or a mixture of these compounds is obtained. However, so far as the purification step of the ester dimer of the present invention is not adversely affected, the production quantity or production ratio of these compounds is not limited.

In the present invention, so long as the compound represented by the formula (II) is obtained, any oxidative esterification method can be adopted. However, oxidation methods preferred from the viewpoint of obtaining high reaction activity are selected from an oxidation method of using a salt containing an oxo ammonium cation of an organic nitroxyl radical and a base, as in NPL 2; and an oxidation method of using a compound selected from an organic nitroxyl radical, an N-hydroxy form thereof, and a salt containing an oxo ammonium cation of them, an oxidizing agent, and a base (hereinafter also referred to as "nitroxyl radical method"), as in NPL 4. From the viewpoint that the yields of the ester dimer are high and the yield of the formyl dioxolane is low, the nitroxyl radical method is preferred. Above all, the oxidation method of using an organic nitroxyl radical and/or an N-hydroxy form thereof, an oxidizing agent, and a base is more preferred.

(Nitroxyl Radical Method)
[Nitroxyl Radical Species]

In the present reaction, as the nitroxyl radical species, a compound selected from an organic nitroxyl radical, an N-hydroxy form thereof, and a salt containing an oxo ammonium cation of them, all of which have oxidation activity with the dioxolane through a combination with an oxidizing agent, can be used.

That is, as the nitroxyl radical species, it is preferred to use at least one compound selected from an organic nitroxyl radical, an N-hydroxy form thereof, and a salt containing an oxo ammonium cation of them.

From the viewpoint that high oxidative esterification activity is obtained, the organic nitroxyl radical is preferably a compound represented by the following formula (VIII), a compound represented by the following formula (IX), or a compound represented by the following formula (X). That is, the nitroxyl radical species is preferably a compound selected from a compound represented by the following formula (VIII), a compound represented by the following formula (IX), or a compound represented by the following formula (X), an N-hydroxy form of them, and a salt containing an oxo ammonium cation of them.

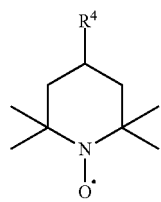

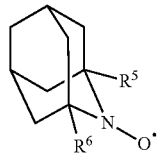

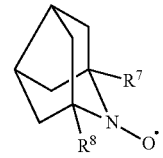

In the formula (VIII), $R^4$ represents a hydrogen atom, a halogen atom, a hydroxy group, an alkoxy group, an acyloxy group, an alkoxycarbonyl group, an amino group, an acylamino group, a sulfonyloxy group, an N-alkylcarbamoyloxy group, a carboxy group, a cyano group, an isocyanato group, an isothiocyanato group, or an oxo group. In the formula (IX), $R^5$ and $R^6$ each independently represent a hydrogen atom or a methyl group. In the formula (X), $R^7$ and $R^8$ each independently represent a hydrogen atom or a methyl group.

In the formula (VIII), $R^4$ represents a hydrogen atom, a halogen atom, a hydroxy group (—OH), an alkoxy group, an acyloxy group, an alkoxycarbonyl group, an amino group, an acylamino group, a sulfonyloxy group, an N-alkylcarbamoyloxy group, a carboxy group (—C(=O)—OH), a cyano group (—C≡N), an isocyanato group (—N=C=O), an isothiocyanato group (—N=C=S), or an oxo group (=O). In the formula (VIII), from the viewpoint of availability and obtaining the ester dimer of the present invention in a high yield, $R^4$ is preferably an alkoxy group, an acyloxy group, or an acylamino group.

Examples of the halogen atom include a fluorine atom, a chlorine atom, a bromine atom, and an iodine atom, and from the viewpoints of easy availability or preparation and low molecular weight, a fluorine atom, a chlorine atom, or a bromine atom is preferred.

The alkoxy group is represented by —$OR^9$, and $R^9$ represents a monovalent hydrocarbon group. From the viewpoints of easy availability or preparation and low molecular weight, $R^9$ is preferably an alkyl group having 1 to 12 carbon atoms, an alkenyl group having 2 to 12 carbon atoms, an alkynyl group having 2 to 12 carbon atoms, or an aryl group having 6 to 20 carbon atoms; more preferably an alkyl group having 1 to 6 carbon atoms, an alkenyl group having 2 to 6 carbon atoms, an alkynyl group having 2 to 6 carbon atoms, or an aryl group having 6 to 14 carbon atoms; still more preferably an alkyl group having 1 to 4 carbon atoms, an alkenyl group having 2 to 4 carbon atoms, an alkynyl group having 2 to 4 carbon atoms, or an aryl group having 6 to 10 carbon atoms; and yet still more preferably a methyl group. In $R^9$, a part of the hydrogen atoms may be substituted with a halogen atom.

The acyloxy group is represented by —O(C=O)—$R^{10}$. From the viewpoints of easy availability or preparation and low molecular weight, $R^{10}$ is preferably a hydrogen atom, an alkyl group having 1 to 12 carbon atoms, an alkenyl group having 1 to 12 carbon atoms, or an aryl group having 6 to 20 carbon atoms; more preferably a hydrogen atom, an alkyl group having 1 to 8 carbon atoms, or an aryl group having 6 to 14 carbon atoms; still more preferably a hydrogen atom, an alkyl group having 1 to 4 carbon atoms, or an aryl group having 6 to 10 carbon atoms; yet still more preferably a methyl group, an ethyl group, or a phenyl group; and even yet still more preferably a phenyl group.

The acylamino group is represented by —NH(C=O)—R". From the viewpoints of easy availability or preparation and low molecular weight, R" is preferably a hydrogen atom, an alkyl group having 1 to 12 carbon atoms, or an aryl group having 6 to 20 carbon atoms; more preferably a hydrogen atom, an alkyl group having 1 to 8 carbon atoms, or an aryl group having 6 to 14 carbon atoms; still more preferably a hydrogen atom, an alkyl group having 1 to 4 carbon atoms, or an aryl group having 6 to 10 carbon atoms; yet still more preferably a methyl group, an ethyl group, or a phenyl group; and even yet still more preferably a methyl group.

The sulfonyloxy group is represented by —O(O=S=O)—$R^{12}$. From the viewpoints of easy availability or preparation and low molecular weight, $R^{12}$ is preferably an alkyl group having 1 to 12 carbon atoms or an aryl group having 6 to 20 carbon atoms; more preferably an alkyl group having 1 to 8 carbon atoms or an aryl group having 6 to 14 carbon atoms; still more preferably an alkyl group having 1 to 4 carbon atoms or an aryl group having 6 to 10 carbon atoms; yet still more preferably a methyl group, an ethyl group, or a p-tolyl group; and even yet still more preferably a methyl group or a p-tolyl group.

Specifically, examples of the nitroxyl radical species include TEMPO, 4-hydroxy-TEMPO, 4-amino-TEMPO, 4-methoxy-TEMPO (hereinafter also referred to as "4-OMe-TEMPO"), 4-ethoxy-TEMPO, 4-phenoxy-TEMPO, 4-acetoxy-TEMPO, 4-benzoyloxy-TEMPO (hereinafter also referred to as "4-OBz-TEMPO"), 4-methacrylate-TEMPO, 4-acetamido-TEMPO (hereinafter also referred to as "4-NHAc-TEMPO"), 4-methylsulfonyloxy-TEMPO (hereinafter also referred to as "4-OMs-TEMPO"), 4-p-toluenesulfonyloxy-TEMPO, 4-oxo-TEMPO, 2-azaadamantane-N-hydroxyl (hereinafter also referred to as "AZADOL" (a trademark, manufactured by Nissan Chemical Industries, Ltd.)), 2-azaadamantane-N-oxyl (hereinafter also referred to as "AZADO"), 1-methyl-2-azaadamantane-N-oxyl (hereinafter also referred to as "1-Me-AZADO"), 9-azanoradamantane-N-oxyl (hereinafter also referred to as "nor-AZADO"), and 1,5-dimethyl-9-azanoradamantane-N-oxyl (hereinafter also referred to as "DMM-AZADO").

From the viewpoints of availability and obtaining the ester dimer of the present invention in a high yield, the nitroxyl radical species is preferably a compound selected from 4-methoxy-TEMPO, 4-benzoyloxy-TEMPO, 4-acetamido-TEMPO, 4-methylsulfonyloxy-TEMPO, and AZADOL, and more preferably a compound selected from 4-benzoyloxy-TEMPO, 4-acetamido-TEMPO, 4-methylsulfonyloxy-TEMPO, and AZADOL.

Though preferred compounds are hereunder exemplified, in the present invention, it should be construed that the nitroxyl radical species is not limited to these compounds.

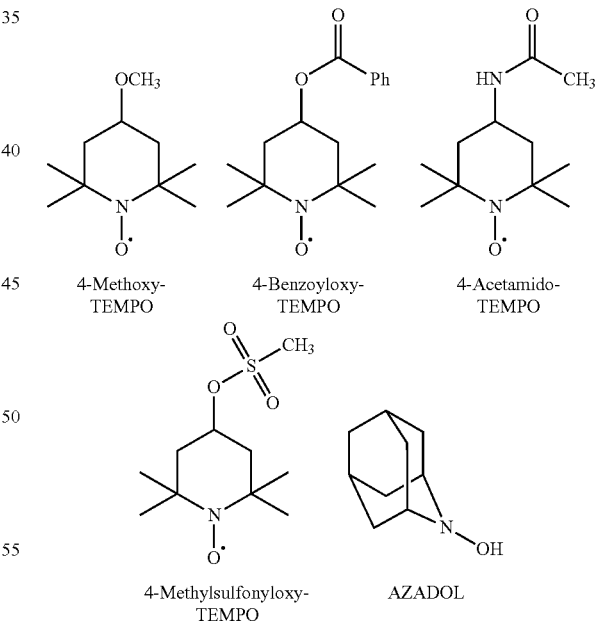

4-Methoxy-TEMPO

4-Benzoyloxy-TEMPO

4-Acetamido-TEMPO

4-Methylsulfonyloxy-TEMPO

AZADOL

From the viewpoint of securing satisfactory oxidation activity, a use amount of the compound selected from an organic nitroxyl radical, an N-hydroxy form thereof, and a salt containing an oxo ammonium cation of them is preferably 0.0001 or more in a molar ratio, more preferably 0.0002 or more in a molar ratio, and still more preferably 0.0005 or more in a molar ratio relative to the dioxolane or the mixture of the dioxolane and dioxane. In addition, from the viewpoint of economy, it is preferably 0.1 or less in a molar ratio, more preferably 0.05 or less in a molar ratio, and still more preferably 0.02 or less in a molar ratio.

[Oxidizing Agent]

In the present reaction, from the viewpoint of reactivity, an oxidizing agent is used together with the nitroxyl radical species. Any oxidizing agent capable of oxidizing the organic nitroxyl radical or an N-hydroxy form thereof into an oxo ammonium cation can be used as the oxidizing agent, and from the viewpoint of suppressing a lowering of the yield due to hydration or hydrolysis of the ester dimer of the present invention, an oxidizing agent composed of a compound containing a halogen, which is capable of being used in an organic solvent (hereinafter also referred to as "halogen-containing oxidizing agent"), is preferred. Examples of the halogen-containing oxidizing agent include an oxidizing agent composed of a compound containing chlorine (hereinafter also referred to as "chlorine-containing oxidizing agent"), such as sodium hypochlorite pentahydrate, meta-chloroperbenzoic acid, trichloroisocyanuric acid (hereinafter also referred to as "TCCA"), tertiary butyl hypochlorite (hereinafter also referred to as "BuOCl"), and N-chlorosuccinimide; an oxidizing agent composed of a compound containing bromine (hereinafter also referred to as "bromine-containing oxidizing agent"), such as N-bromosuccinimide; and a halogen-containing oxidizing agent having plural halogen elements, such as (dichloroiodo) benzene. From the viewpoint of obtaining the ester dimer of the present invention in a high yield and the viewpoints of stability, safety, and easiness of handling of the oxidizing agent, the halogen-containing oxidizing agent is preferably a chlorine-containing oxidizing agent, and more preferably an oxidizing agent selected from TCCA and tBuOCl, with TCCA being still more preferred from the viewpoint of availability.

As the oxidizing agent of the present invention, an oxoammonium cation of an organic nitroxyl radical or an N-hydroxy form thereof, including an oxoammonium cation resulting from one electron oxidation of the compound represented by the formula (VIII), the compound represented by the formula (IX), or the compound represented by the formula (X), is excluded.

From the viewpoints of making both high reaction conversion of the dioxolane or the mixture of the dioxolane and the dioxane and suppression of production amount of the formyl dioxolane compatible with each other, a molar ratio of the oxidation active species relative to the dioxolane or the mixture of the dioxolane and the dioxane is preferably 1.0 or more, and more preferably 1.1 or more. In addition, from the viewpoints of economy and reduction of waste amount, the molar ratio is preferably 2.0 or less, and more preferably 1.5 or less.

The oxidation active species means a chlorine atom in the case of the chlorine-containing oxidizing agent, and in the case of TCCA, 3 moles of the oxidation active species is existent in one mole of the molecule.

[Base]

In the present reaction, a base is used for the purpose of neutralizing an acid by-produced due to consumption of the oxidizing agent, or other purpose. Any base can be used unless it directly causes a side-reaction with the dioxolane or the mixture of the dioxolane and the dioxane, the catalyst, or the oxidizing agent to impair the target oxidation reaction, and a heterocyclic aromatic amine having a pyridine skeleton is preferred from the viewpoints that it is weakly basic and that a side-reaction is suppressed. For the purpose of suppressing the use amount, the heterocyclic aromatic amine having a pyridine skeleton may be used in combination with an inorganic base, and from the viewpoint of obtaining the ester dimer in a high yield, the heterocyclic aromatic amine having a pyridine skeleton is preferably used alone.

Examples of the heterocyclic aromatic amine having a pyridine skeleton include pyridine, an alkyl-substituted pyridine, a polycyclic quinoline, and a bipyridyl that is a pyridine dimer. Specifically, examples thereof include pyridine, 2-methylpyridine, 3-methylpyridine, 4-methylpyridine, 2-ethylpyridine, 3-ethylpyridine, 4-ethylpyridine, 2,6-lutidine, 3,5-lutidine, 2,3,5-collidine, 2,4,6-collidine, 5-ethyl-2-methylpyridine, 3,5-diethylpyridine, 2,2'-bipyridyl, 2,4'-bipyridyl, 4,4'-bipyridyl, and quinoline.

Among the heterocyclic aromatic amines having a pyridine skeleton, it is preferred to select and use a heterocyclic aromatic amine having a pyridine skeleton, which is large in a difference of boiling point from the dioxanone or the ester dimer of the present invention, and which is easily separated through distillation. From the viewpoint of availability, an amine selected from pyridine and 5-ethyl-2-methylpyridine is preferred; from the viewpoint of easiness of recovery on regenerating an amine from an amine salt after completion of the reaction, a water-insoluble heterocyclic aromatic amine having a pyridine skeleton is preferred; and from the viewpoint of yield, an amine selected from pyridine, 3,5-lutidine, 2,6-lutidine, 3-ethylpyridine, 4-ethylpyridine, and 5-ethyl-2-methylpyridine is preferred, and an amine selected from pyridine, 3,5-lutidine, 3-ethylpyridine, 4-ethylpyridine, and 5-ethyl-2-methylpyridine is more preferred.

From the viewpoint of completely neutralizing an oxidizing agent-derived acid to suppress the decomposition of an acetal group of the dioxolane and the ester dimer of the present invention, a molar ratio of the base relative to the dioxolane or the mixture of the dioxolane and the dioxane is preferably 1.0 or more, more preferably 1.1 or more, still more preferably 1.2 or more, and yet still more preferably 1.3 or more. In addition, from the viewpoints of economy and easiness of recovery of the excessive base, the molar ratio is preferably 2.5 or less, more preferably 2.0 or less, and still more preferably 1.7 or less.

[Solvent]

In the present reaction, it is possible to carry out the reaction under a non-solvent or solvent-used condition. In the case where the oxidizing agent to be used or an oxidizing agent-derived reduced product or salt, which is by-produced at the time of reaction, is a solid, from the viewpoints of dissolving the solid and decreasing the viscosity of the reaction solution to make it easy to perform stirring, the solvent-used condition is preferred. Any solvent can be used so far as it is inert against the dioxolane or the mixture of the dioxane and the dioxolane, the oxidizing agent, and the base, and in the case of using TCCA as the oxidizing agent, from the viewpoint of solubility of TCCA and availability, a solvent selected from acetone, 2-butanone, cyclopentanone, acetonitrile, and dichloromethane is preferred; a solvent selected from acetone, 2-butanone, acetonitrile, and dichloromethane is more preferred; and a solvent selected from acetone and 2-butanone is still more preferred. In addition, from the viewpoint of productivity of the ester dimer of the present invention, acetonitrile is still more preferred.

The solvent may be used alone or may be used in combination of two or more thereof.

The use amount of the solvent is not particularly limited, and from the viewpoint of operability and the viewpoint of obtaining the ester dimer of the present invention in a high yield, the use amount of the solvent relative to the whole of the reaction system is preferably 20% by mass or more, more preferably 30% by mass or more, still more preferably 40% by mass or more, yet still more preferably 50% by mass or more, and even yet still more preferably 60% by mass or more, and from the viewpoint of productivity, the use amount of the solvent relative to the whole of the reaction system is preferably 90% by mass or less, more preferably 85% by mass or less, and still more preferably 80% by mass or less.

[Reaction Procedures]

In the present reaction, the charging order of the respective raw materials, and the like are not limited, since the reaction is an exothermic oxidation reaction, from the viewpoints of easiness of temperature control of the reaction solution and safety, a method of dropping the oxidizing agent or oxidizing agent solution to the mixture or the mixed solution containing the raw materials other than the oxidizing agent is preferred.

From the viewpoint of suppressing a facility load and a rise of viscosity of the reaction solution, a temperature of the reaction solution during dropping of the oxidizing agent or oxidizing agent solution is preferably −15° C. or higher, and more preferably −10° C. or higher. In addition, from the viewpoint of suppressing a side-reaction, such as decomposition at a high temperature, to obtain the ester dimer of the present invention in a high yield, the temperature of the reaction solution is preferably 25° C. or lower, and more preferably 10° C. or lower. After completion of dropping of the oxidizing agent or oxidizing agent solution, the reaction is continued until the dioxolane all react, or a lowering of the residual amount stops. From the viewpoint of promoting the reaction of the dioxolane, the temperature of the reaction solution is preferably −10° C. or higher, and more preferably −5° C. or higher, and from the viewpoint of suppressing a side-reaction, it is preferably 50° C. or lower, and more preferably 30° C. or lower.

At the time of completion of the reaction, from the viewpoints of suppression of a side-reaction and safety, it is preferred to add a reaction terminator that completely consumes the residual oxidizing agent. As the reaction terminator, any compound can be used so far as it reacts with the oxidizing agent and hardly reacts with the oxidation product, such as the ester dimer of the present invention, and; however, from the viewpoints of availability and making it easy to purify the ester dimer of the present invention, an alcohol is preferred. The alcohol is preferably a primary or secondary alcohol, and from the viewpoint of suppressing ester interchange with the ester dimer of the present invention, the alcohol is more preferably a secondary alcohol. In addition, an alcohol having 1 or more and 12 or less carbon atoms is preferred.

The addition amount of the reaction terminator is not particularly limited.

[Separation of Compound Represented by Formula (I)]

In the present invention, it is preferred to include a step of separating the ester dimer of the present invention (compound represented by the formula (II)) after the step of oxidatively esterifying the dioxolane or preferably the mixture of dioxolane and the dioxane.

In the step of spearing the ester dimer of the present invention, from the viewpoint of efficiency, it is preferred that the solid, such as the salt or the reduced product of the oxidizing agent, is separated by means of filtration or oil-water extraction, and that the dioxanone, the formyl dioxolane and the residual base are separated by means of distillation or column chromatography. With respect to the water-soluble by-product, such as the salt or the reduced product of the oxidizing agent, from the viewpoint of efficiency of the removal, it is preferred to perform a water-washing step of removing the water-soluble by-product by means of water washing. With respect to the removal of the water-soluble by-product, the water-washing step and the filtration step may be jointly adopted, or only the water-washing step may be performed.

For the separation between the dioxanone and the ester dimer of the present invention, from the viewpoint of making it possible to easily perform the separation utilizing a large difference in boiling point, the separation by means of distillation is more preferred. It is possible to carry out the separation by means of distillation under either simple distillation conditions or rectification conditions, and from the viewpoint of obtaining the high-purity ester dimer of the present invention in a high distillation yield, it is preferred to perform the separation under rectification conditions. As for the rectification conditions, from the viewpoint of highly purifying the ester dimer of the present invention, the number of theoretical stages of a rectifying tower is preferably 2 stages or more, and more preferably 5 stages or more, and a reflux ratio is preferably 0.1 or more, and more preferably 0.5 or more. In addition, from the viewpoint of purification productivity of the ester dimer of the present invention, the number of theoretical stages of the rectifying tower is preferably 20 stages or less, and more preferably 10 stages or less, and the reflux ratio is preferably 20 or less, and more preferably 10 or less.

The novel glyceric acid ester of the present invention (ester dimer of the present invention) is a glyceric acid ester in which hydroxy groups at the 2-position and 3-position are protected as a cyclic acetal group and is useful as synthetic intermediates for glyceric acid, a glyceric acid salt, a deprotected glyceric acid ester, and the like, which are used as raw materials for various medicaments, cosmetics, detergents, polymers and the like.

[Production Method of Glyceric Acid, Glyceric Acid Salt, or Deprotected Glyceric Acid Ester]

Glyceric acid, a glyceric acid salt, or a deprotected glyceric acid ester can be produced through hydrolysis or alcoholysis of the acetal group and the ester group of the above-obtained ester dimer of the present invention. Though the hydrolysis or alcoholysis method is not particularly limited, a method of performing the decomposition with an excessive amount of water or an alcohol in the presence of an acid catalyst is the easiest and preferred.

The alcohol which is used for the alcoholysis is preferably a primary alcohol from the viewpoint of reactivity (in particular, decomposition of the acetal group), and more preferably a primary alcohol having 1 or more and 3 or less carbon atoms from the viewpoint that a boiling point of the deprotected glyceric acid ester is low and readily subjected to distillation purification.

From the viewpoint that the polarity of the deprotected glyceric acid ester is thoroughly decreased, thereby allowing the deprotected glyceric acid ester and glycerin to be readily separated and purified by an oil-water extraction method, a linear or branched primary alcohol having 4 or more and 8 or less carbon atoms is more preferred.

The resulting glyceric acid, glyceric acid salt, or deprotected glyceric acid ester is separated from the by-product (glycerin, aldehyde, or an acetal thereof) preferably by means of distillation, column chromatography, or the like.

The present invention further discloses the following [1] to [40].

[1] A method of producing a compound represented by the following formula (II), including a step of oxidatively esterifying a compound represented by the following formula (I).

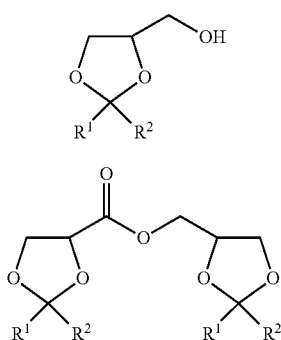

(I)

(II)

In the formulae (I) and (II), $R^1$ and $R^2$ each independently represent a hydrogen atom or a monovalent hydrocarbon group, or $R^1$ and $R^2$ are bonded to each other to form a divalent hydrocarbon group for constituting a ring structure, provided that the case where $R^1$ and $R^2$ are a methyl group at the same time is excluded.

[2] The production method as set forth in [1], including a step of oxidatively esterifying a mixture of a compound represented by the following formula (I) and a compound represented by the following formula (V).

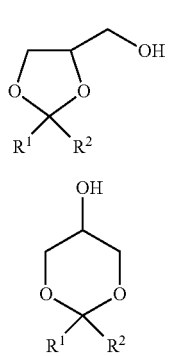

(I)

(V)

In the formulae (I) and (V), $R^1$ and $R^2$ each independently represent a hydrogen atom or a monovalent hydrocarbon group, or $R^1$ and $R^2$ are bonded to each other to form a divalent hydrocarbon group for constituting a ring structure, provided that the case where $R^1$ and $R^2$ are a methyl group at the same time is excluded.

[3] The production method as set forth in [2], wherein the mixture of the compound represented by the formula (I) and the compound represented by the formula (V) is produced by a method of acetalizing glycerol and a compound represented by the following formula (III) or a multimer thereof in the presence of an acid catalyst (method 1), or subjecting glycerol and a compound represented by the following formula (IV) to acetal exchange in the presence of an acid catalyst (method 2).

<Method 1>

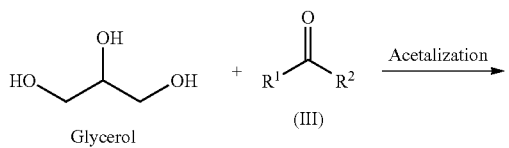

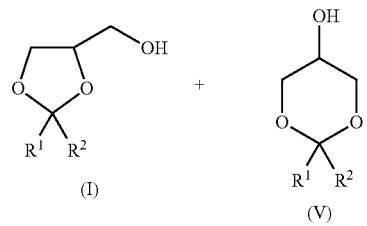

(I)

(V)

<Method 2>

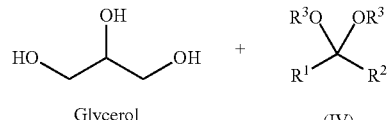

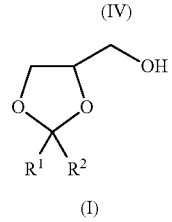

(I)

(V)

In the formulae, $R^1$ and $R^2$ each independently represent a hydrogen atom or a monovalent hydrocarbon group, or $R^1$ and $R^2$ are bonded to each other to form a divalent hydrocarbon group for constituting a ring structure, provided that the case where $R^1$ and $R^2$ are a methyl group at the same time is excluded, and $R^3$'s each independently represent a monovalent hydrocarbon group, preferably a hydrocarbon group having 1 or more and 8 or less carbon atoms, more preferably a monovalent hydrocarbon group having 1 or more and 3 or less carbon atoms, still more preferably a monovalent alkyl group having 1 or more and 3 or less carbon atoms, and yet still more preferably a methyl group.

[4] The production method as set forth in [2] or [3], including the following step 1 and step 2.

Step 1: A step of acetalizing glycerol and a compound represented by the following formula (III) or a multimer thereof in the presence of an acid catalyst (step 1-1), or a step of subjecting glycerol and a compound represented by the following formula (IV) to acetal exchange in the presence of an acid catalyst (step 1-2)

Step 2: A step of oxidatively esterifying a mixture of a compound represented by the following formula (I) and a compound represented by the following formula (V)

<Step 1-1>

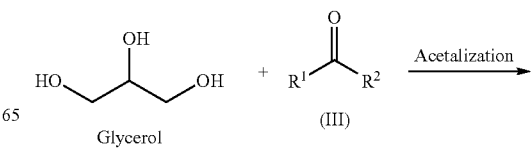

-continued

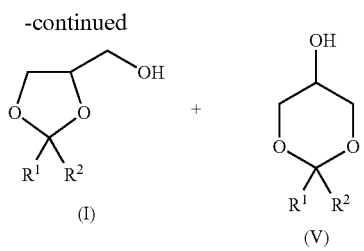

(I) + (V)

<Step 1-2>

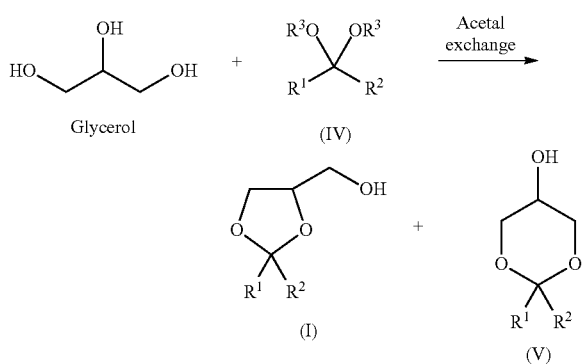

In the formulae, $R^1$ and $R^2$ each independently represent a hydrogen atom or a monovalent hydrocarbon group, or $R^1$ and $R^2$ are bonded to each other to form a divalent hydrocarbon group for constituting a ring structure, provided that the case where $R^1$ and $R^2$ are a methyl group at the same time is excluded, and $R^3$'s each independently represent a monovalent hydrocarbon group, preferably a hydrocarbon group having 1 or more and 8 or less carbon atoms, more preferably a monovalent hydrocarbon group having 1 or more and 3 or less carbon atoms, still more preferably a monovalent alkyl group having 1 or more and 3 or less carbon atoms, and yet still more preferably a methyl group.

[5] The production method as set forth in any of [1] to [4], wherein preferably, $R^1$ and $R^2$ are each a monovalent hydrocarbon group having 1 or more and 8 or less carbon atoms; more preferably, $R^1$ is a monovalent hydrocarbon group having 1 or more and 8 or less carbon atoms, and $R^2$ is a monovalent hydrocarbon group having 2 or more and 8 or less carbon atoms; still more preferably, $R^1$ is an alkyl group having 1 or more and 8 or less carbon atoms, and $R^2$ is an alkyl group having 2 or more and 8 or less carbon atoms; yet still more preferably, $R^1$ is an alkyl group having 1 or 2 carbon atoms, and $R^2$ is an alkyl group having 2 or more and 6 or less carbon atoms; even yet still more preferably, $R^1$ is an alkyl group having 1 or 2 carbon atoms, and $R^2$ is an alkyl group having 2 or more and 4 or less carbon atoms; and even yet still more preferably $R^1$ is a methyl group, and $R^2$ is an ethyl group.

[6] The production method as set forth in any of [1] to [4], wherein $R^1$ and $R^2$ are bonded to each other to form a divalent hydrocarbon group for constituting a ring structure; $R^1$ and $R^2$ are preferably bonded to each other to form a divalent hydrocarbon group having 2 or more and 7 or less carbon atoms, more preferably a divalent hydrocarbon group having 3 or more and 6 or less carbon atoms, still more preferably a divalent hydrocarbon group having 4 or more and 5 or less carbon atoms, yet still more preferably a divalent hydrocarbon group having 5 carbon atoms.

[7] The production method as set forth in any of [1] to [4], wherein $R^2$ is a hydrogen atom; $R^1$ is preferably a hydrogen atom or a monovalent hydrocarbon group having 1 or more and 20 or less carbon atoms; the hydrocarbon group is preferably an alkyl group or an aryl group; the carbon number of the alkyl group is preferably 1 or more, and it is preferably 20 or less, more preferably 18 or less, still more preferably 16 or less, yet still more preferably 14 or less, yet still more preferably 12 or less, yet still more preferably 10 or less, yet still more preferably 8 or less, yet still more preferably 6 or less, yet still more preferably 4 or less, and yet still more preferably 2 or less; such an alkyl group may be either linear or branched; and the carbon number of the aryl group is preferably 6 or more, and it is preferably 20 or less, more preferably 18 or less, still more preferably 16 or less, yet still more preferably 14 or less, yet still more preferably 12 or less, yet still more preferably 10 or less, yet still more preferably 8 or less, and yet still more preferably 6 or less.

[8] The production method as set forth in any of [1] to [4], wherein $R^2$ is a hydrogen atom; and $R^1$ is preferably a hydrogen atom or a monovalent hydrocarbon group having 1 or more and 20 or less carbon atoms, more preferably a hydrogen atom or a linear alkyl group having 1 or more and 8 or less carbon atoms, a branched alkyl group having 1 or more and 8 or less carbon atoms, or an aryl group having a carbon umber of 6 or more and 20 or less carbon atoms, still more preferably a hydrogen atom, a methyl group, or a phenyl group, and yet still more preferably a hydrogen atom.

[9] The production method as set forth in any of [1] to [8], wherein a yield of the formyl dioxolane produced from the compound represented by the formula (I) is preferably 20% or less, more preferably 10% or less, still more preferably 5% or less, yet still more preferably substantially 0%, and even yet still more preferably 0%.

[10] The production method as set forth in any of [1] to [9], wherein in the step of performing oxidative esterification, an oxidative esterification method selected from an oxidative esterification method of using a salt containing an oxo ammonium cation of an organic nitroxyl radical and a base; and an oxidative esterification method of using a compound selected from an organic nitroxyl radical, an N-hydroxy form thereof, and a salt containing an oxo ammonium cation of them, an oxidizing agent, and a base (hereinafter also referred to as "nitroxyl radical method") is preferably adopted.

[11] The production method as set forth in [10], wherein the organic nitroxyl radical is a compound represented by the following formula (VIII), a compound represented by the following formula (IX), or a compound represented by the following formula (X).

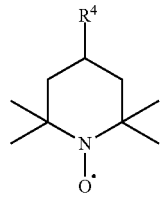

(VIII)

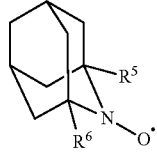

(IX)

-continued

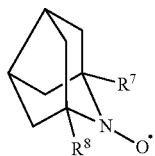
(X)

In the formula (VIII), $R^4$ represents a hydrogen atom, a halogen atom, a hydroxy group, an alkoxy group, an acyloxy group, an alkoxycarbonyl group, an amino group, an acylamino group, a sulfonyloxy group, an N-alkylcarbamoyloxy group, a carboxy group, a cyano group, an isocyanato group, an isothiocyanato group, or an oxo group, and preferably an alkoxy group, an acyloxy group, or an acylamino group. In the formula (IX), $R^5$ and $R^6$ each independently represent a hydrogen atom or a methyl group. In the formula (X), $R^7$ and $R^8$ each independently represent a hydrogen atom or a methyl group.

[12] The production method as set forth in [10] or [11], wherein at least one compound selected from the organic nitroxyl radical, an N-hydroxy form thereof, and a salt containing an oxo ammonium cation of them is preferably TEMPO, 4-hydroxy-TEMPO, 4-amino-TEMPO, 4-methoxy-TEMPO (hereinafter also referred to as "4-OMe-TEMPO"), 4-ethoxy-TEMPO, 4-phenoxy-TEMPO, 4-acetoxy-TEMPO, 4-benzoyloxy-TEMPO (hereinafter also referred to as "4-OBz-TEMPO"), 4-methacrylate-TEMPO, 4-acetamido-TEMPO (hereinafter also referred to as "4-NHAc-TEMPO"), 4-methylsulfonyloxy-TEMPO (hereinafter also referred to as "4-OMs-TEMPO"), 4-p-toluenesulfonyloxy-TEMPO, 4-oxo-TEMPO, 2-azaadamantane-N-hydroxy (hereinafter also referred to as "AZADOL"), 2-azaadamantane-N-oxyl (hereinafter also referred to as "AZADO"), 1-methyl-2-azaadamantane-N-oxyl (hereinafter also referred to as "1-Me-AZADO"), 9-azanoradamantane-N-oxyl (hereinafter also referred to as "nor-AZADO"), or 1,5-dimethyl-9-azanoradamantane-N-oxyl (hereinafter also referred to as "DMM-AZADO"); more preferably a compound selected from 4-methoxy-TEMPO, 4-benzoyloxy-TEMPO, 4-acetamido-TEMPO, 4-methylsulfonyloxy-TEMPO, and AZADOL; and still more preferably a compound selected from 4-benzoyloxy-TEMPO, 4-acetamido-TEMPO, 4-methylsulfonyloxy-TEMPO, and AZADOL.

[13] The production method as set forth in any of [10] to [12], wherein a use amount of the compound selected from the organic nitroxyl radical, an N-hydroxy form thereof, and a salt containing an oxo ammonium cation of them is preferably 0.0001 or more in a molar ratio, more preferably 0.0002 or more in a molar ratio, and still more preferably 0.0005 or more in a molar ratio, and it is preferably 0.1 or less in a molar ratio, more preferably 0.05 or less in a molar ratio, and still more preferably 0.02 or less in a molar ratio, relative to the compound represented by the formula (I) or the mixture of the compound represented by the formula (I) and the compound represented by the formula (V).

[14] The production method as set forth in any of [10] to [13], wherein the oxidizing agent is preferably an oxidizing agent composed of a compound containing a halogen (halogen-containing oxidizing agent), more preferably an oxidizing agent composed of a compound containing chlorine (chlorine-containing oxidizing agent), still more preferably an oxidizing agent selected from trichloroisocyanuric acid and tertiary butyl hypochlorite, and yet still more preferably trichloroisocyanuric acid.

[15] The production method as set forth in any of [10] to [14], wherein a molar ratio of the oxidation active species of the oxidizing agent relative to the compound represented by the formula (I) or the mixture of the compound represented by the formula (I) and the compound represented by the formula (V) is preferably 1.0 or more, and more preferably 1.1 or more, and it is preferably 2.0 or less, and more preferably 1.5 or less.

[16] The production method as set forth in any of [10] to [15], wherein the base is a heterocyclic aromatic amine having a pyridine skeleton.

[17] The production method as set forth in [16], wherein the heterocyclic aromatic amine having a pyridine skeleton is preferably at least one selected from pyridine, 2-methylpyridine, 3-methylpyridine, 4-methylpyridine, 2-ethylpyridine, 3-ethylpyridine, 4-ethylpyridine, 2,6-lutidine, 3,5-lutidine, 2,3,5-collidine, 2,4,6-collidine, 5-ethyl-2-methylpyridine, 3,5-diethylpyridine, 2,2'-bipyridyl, 2,4'-bipyridyl, 4,4'-bipyridyl, and quinoline; more preferably at least one selected from pyridine, 3,5-lutidine, 2,6-lutidine, 3-ethylpyridine, 4-ethylpyridine, and 5-ethyl-2-methylpyridine; and still more preferably at least one selected from pyridine, 3,5-lutidine, 3-ethylpyridine, 4-ethylpyridine, and 5-ethyl-2-methylpyridine.

[18] The production method as set forth in any of [10] to [17], wherein a molar ratio of the base relative to the compound represented by the formula (I) or the mixture of the compound represented by the formula (I) and the compound represented by the formula (V) is preferably 1.0 or more, more preferably 1.1 or more, still more preferably 1.2 or more, and yet still more preferably 1.3 or more, and it is preferably 2.5 or less, more preferably 2.0 or less, and still more preferably 1.7 or less.

[19] The production method as set forth in any of [1] to [18], wherein in the step of performing oxidative esterification, a solvent is preferably used, and the solvent is preferably a solvent selected from acetone, 2-butanone, cyclopentanone, acetonitrile, and dichloromethane; more preferably a solvent selected from acetone, 2-butanone, acetonitrile, and dichloromethane; and still more preferably a solvent selected from acetone and 2-butanone.

[20] The production method as set forth in [19], wherein the use amount of the solvent relative to the whole of the reaction system is preferably 20% by mass or more, more preferably 30% by mass or more, still more preferably 40% by mass or more, yet still more preferably 50% by mass or more, and yet still more preferably 60% by mass or more, and it is preferably 90% by mass or less, more preferably 85% by mass or less, and still more preferably 80% by mass or less.

[21] The production method as set forth in any of [10] to [20], wherein in the step of performing oxidative esterification, the oxidizing agent or oxidizing agent solution is preferably added to the mixture or the mixed solution containing the raw materials other than the oxidizing agent.

[22] The production method as set forth in [21], wherein a temperature of the reaction solution during dropping of the oxidizing agent or oxidizing agent solution is preferably −15° C. or higher, and more preferably −10° C. or higher, and it is preferably 25° C. or lower, and more preferably 10° C. or lower.

[23] The production method as set forth in [21] or [22], wherein after completion of dropping of the oxidizing agent or oxidizing agent solution, the reaction is continued until the dioxolane all reacts, or a lowering of the residual amount stops.

[24] The production method as set forth in [23], wherein the temperature of the reaction solution is preferably −10° C. or higher, and more preferably −5° C. or higher, and it is preferably 50° C. or lower, and more preferably 30° C. or lower.
[25] The production method as set forth in any of [1] to [24], wherein an alcohol is preferably used as a reaction terminator.
[26] The production method as set forth in [25], wherein the reaction terminator is preferably a primary or secondary alcohol, and more preferably a secondary alcohol.
[27] The production method as set forth in [25] or [26], wherein the reaction terminator is preferably an alcohol having 1 or more and 12 or less carbon atoms.
[28] The production method as set forth in any of [1] to [27], wherein the method includes, after the step of oxidatively esterifying the compound represented by the formula (I), and preferably the mixture of the compound represented by the formula (I) and the compound represented by the formula (V), a step of separating the compound represented by the formula (II).
[29] The production method as set forth in [28], wherein the separation in the step of separating the compound represented by the formula (II) is separation through distillation.
[30] The production method as set forth in [29], wherein the separation through distillation is preferably performed under rectification conditions.
[31] The production method as set forth in [30], wherein as for the rectification conditions, the number of theoretical stages of a rectifying tower is preferably 2 stages or more, and more preferably 5 stages or more, and a reflux ratio is preferably 0.1 or more, and more preferably 0.5 or more; and the number of theoretical stages of the rectifying tower is preferably 20 stages or less, and more preferably 10 stages or less, and the reflux ratio is preferably 20 or less, and more preferably 10 or less.
[32] A method of producing glyceric acid, a glyceric acid salt, or a deprotected glyceric acid ester, including subjecting the compound represented by the formula (II) as separated in any of [28] to [31] to hydrolysis or alcoholysis.
[33] A method of producing glyceric acid, a glyceric acid salt, or a deprotected glyceric acid ester, including a step of producing the compound represented by the formula (II) by the production method of any of [1] to [31]; and a step of subjecting the compound represented by the formula (II), which is produced in the foregoing step, to hydrolysis or alcoholysis.
[34] The production method as set forth in [32] or [33], wherein the alcohol to be used for the alcoholysis is preferably a primary alcohol, and more preferably a primary alcohol having 1 or more and 3 or less carbon atoms.
[35] The production method as set forth in [32] or [33], wherein the alcohol to be used for the alcoholysis is more preferably a linear or branched primary alcohol having 4 or more and 8 or less carbon atoms.
[36] A compound represented by the following formula (II).

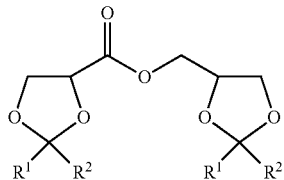

(II)

In the formula (II), $R^1$ and $R^2$ each independently represent a hydrogen atom or a monovalent hydrocarbon group, or $R^1$ and $R^2$ are bonded to each other to form a divalent hydrocarbon group for constituting a ring structure, provided that the case where $R^1$ and $R^2$ are a methyl group at the same time is excluded.
[37] The compound as set forth in [36], wherein preferably, $R^1$ and $R^2$ are each a monovalent hydrocarbon group having 1 or more and 8 or less carbon atoms; more preferably, $R^1$ is a monovalent hydrocarbon group having 1 or more and 8 or less carbon atoms, and $R^2$ is a monovalent hydrocarbon group having 2 or more and 8 or less carbon atoms; still more preferably, $R^1$ is an alkyl group having 1 or more and 8 or less carbon atoms, and $R^2$ is an alkyl group having 2 or more and 8 or less carbon atoms; yet still more preferably, $R^1$ is an alkyl group having 1 or 2 carbon atoms, and $R^2$ is an alkyl group having 2 or more and 6 or less carbon atoms; even yet still more preferably, $R^1$ is an alkyl group having 1 or 2 carbon atoms, and $R^2$ is an alkyl group having 2 or more and 4 or less carbon atoms; and even still more preferably, $R^1$ is a methyl group, and $R^2$ is an ethyl group.
[38] The compound as set forth in [36], wherein $R^1$ and $R^2$ are bonded to each other to form a divalent hydrocarbon group for constituting a ring structure; $R^1$ and $R^2$ are preferably bonded to each other to form a divalent hydrocarbon group having 2 or more and 7 or less carbon atoms, more preferably a divalent hydrocarbon group having 3 or more and 6 or less carbon atoms, still more preferably a divalent hydrocarbon group having 4 or more and 5 or less carbon atoms, yet still more preferably a divalent hydrocarbon group having 5 carbon atoms.
[39] The compound as set forth in [36], wherein $R^2$ is a hydrogen atom; $R^1$ is preferably a hydrogen atom or a monovalent hydrocarbon group having 1 or more and 20 or less carbon atoms; the hydrocarbon group is preferably an alkyl group or an aryl group; the carbon number of the alkyl group is preferably 1 or more, and it is preferably 20 or less, more preferably 18 or less, still more preferably 16 or less, yet still more preferably 14 or less, yet still more preferably 12 or less, yet still more preferably 10 or less, yet still more preferably 8 or less, yet still more preferably 6 or less, yet still more preferably 4 or less, and yet still more preferably 2 or less; such an alkyl group may be either linear or branched; and the carbon number of the aryl group is preferably 6 or more, and it is preferably 20 or less, more preferably 18 or less, still more preferably 16 or less, yet still more preferably 14 or less, yet still more preferably 12 or less, yet still more preferably 10 or less, yet still more preferably 8 or less, and yet still more preferably 6 or less.
[40] The compound as set forth in [36], wherein $R^2$ is a hydrogen atom; and $R^1$ is preferably a hydrogen atom or a monovalent hydrocarbon group having 1 or more and 20 or less carbon atoms, more preferably a hydrogen atom or a linear alkyl group having 1 or more and 8 or less carbon atoms, a branched alkyl group having 1 or more and 8 or less carbon atoms, or an aryl group having a carbon umber of 6 or more and 20 or less carbon atoms, still more preferably a hydrogen atom, a methyl group, or a phenyl group, and yet still more preferably a hydrogen atom.

EXAMPLES

[Identification of Compound]
Each of compounds obtained in the following Production Examples, Examples, or Comparative Examples (hereinafter also referred to as "Examples and the like") was identified through spectral analysis with a nuclear magnetic resonance apparatus (NMR, manufactured by Agilent Technologies, model: Agilent 400-MR DD2), an infrared spectrophotometer (IR, manufactured by Horiba, Ltd., model: FT-710), and a gas chromatography mass spectrometer (GC-MS, manufactured by Agilent Technologies, model: Agilent 5975C).

[Purity of Compound Produced or Purified]

The purity of each of compounds produced or purified in the following Examples and the like was determined through analysis (GC analysis) with a gas chromatograph (manufactured by Agilent Technologies, model: Agilent 6850). The term "%" regarding the purity means "GC %", and this value was used at the time of expressing in terms of a net quantity regarding the reaction raw materials and high-purity authentic samples.

[Unit, Conversion, and Yield]

The conversion of each of reaction raw materials and the yield of each of products shown in the following Examples and the like were determined through internal standard method quantitative GC analysis. A calibration curve necessary for the quantitative analysis was prepared using a commercially available authentic sample, or a high-purity authentic sample purified from a reaction mixture through distillation or silica gel column chromatography. However, the yield of a formyl dioxolane was calculated by substituting a calibration curve of a corresponding dioxanone.

[Measurement Conditions of GC and GC-MS]

Column: Ultra ALLOY-1 (MS/HT) (Frontier Laboratories Ltd. a trademark, inner diameter: 0.25 mm, film thickness: 0.15 μm, length: 30 m)

Carrier gas: Helium, 1.0 mL/min

Injection conditions: 250° C., split ratio: 1/50

Detection conditions: FID system, 220° C.

Column temperature conditions: After holding at 40° C. for 5 minutes, the temperature is raised to 350° C. at 10° C./min.

Internal standard compound: n-Dodecane

Ionization mode: EI

Ion source temperature: 230° C.

Interface temperature: 350° C.

Production Examples: Production of 2,2-dialkyl-4-hydroxymethyl-2-methyl-1,3-dioxolane as a raw material The reaction which was performed in the Production Examples is as follows.

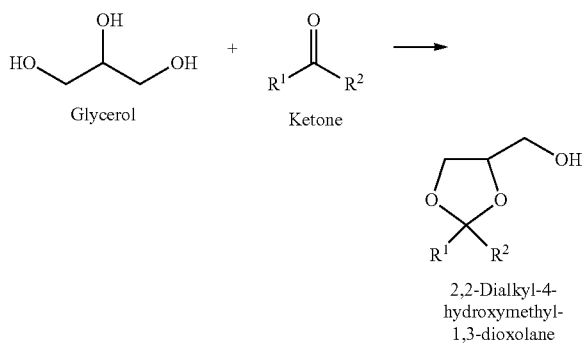

Production Example 1-1: Production of 2-ethyl-4-hydroxymethyl-2-methyl-1,3-dioxolane ($R^1$=Me, $R^2$=Et) as a raw material In a one-liter flask equipped with a Dean-Stark apparatus, 184 g of glycerol (purity: 100%, 2.00 mol), 162 g of 2-butanone (purity: 98.0%, 2.20 mol), 981 mg of methanesulfonic acid (purity: 98.0%, 10.0 mol), and 50 g of n-hexane were charged and refluxed for 5 hours while removing water by-produced by the reaction outside the reaction system. After cooling, the resultant was neutralized with 3.50 g of a 20% ethanol solution of sodium ethoxide (700 mg, 10.3 mmol as sodium ethoxide). As a result of GC analysis of the reaction solution, a reaction yield of a cis- and trans-isomer mixture of 2-ethyl-4-hydroxymethyl-2-methyl-1,3-dioxolane was 74%.

Subsequently, the reaction solution was transferred into a 500-mL flask equipped with a Claisen head; after heating at 50° C., the pressure was gradually reduced to distill off the n-hexane and ethanol; and simple distillation was further performed under reduced pressure of 0.13 kPa (absolute pressure), thereby obtaining 220 g of a stereoisomer mixture which was distilled out as a colorless liquid at a fraction temperature of 91 to 94° C. The purity was 95.3%, and the distillation yield was 97%.

<Spectral Data of Stereoisomer Mixture>

IR (neat, cm$^{-1}$): 3465 (br), 2973, 2935, 2883, 1466, 1375, 1190, 1078, 1041, 876

MS (m/z): 131, 117, 57, 43

Production Example 1-2: Production of 2-isobutyl-4-hydroxymethyl-2-methyl-1,3-dioxolane ($R^1$=Me, $R^2$=$^i$Bu) as a raw material Using 221 g of 4-methyl-2-pentanone (purity: 99.5%, 2.20 mol) as a reaction raw material, the same operations as in Production Example 1-1 were followed, thereby obtaining a cis- and trans-isomer mixture of 2-isobutyl-4-hydroxymethyl-2-methyl-1,3-dioxolane in a reaction yield of 68%.

Simple distillation was further performed under reduced pressure of 0.13 kPa (absolute pressure), thereby obtaining 246 g of a stereoisomer mixture which was distilled out as a colorless liquid at a fraction temperature of 117 to 123° C. The purity was 97.4%, and the distillation yield was 92%.

<Spectral Data of Stereoisomer Mixture>

IR (neat, cm$^{-1}$): 3446 (br), 2952, 2871, 1466, 1375, 1184, 1090, 1041

MS (m/z): 159, 143, 117, 99, 85, 57, 43

Production Example 1-3: Production of 2-hydroxymethyl-1,4-dioxaspiro[4.5]decane ($R^1$ and $R^2$=—(CH$_2$)$_5$—) as a raw material Using 218 g of cyclohexanone (purity: 99.0%, 2.20 mol) as a reaction raw material, the same operations as in Production Example 1-1 were followed, thereby obtaining 2-hydroxymethyl-1,4-dioxaspiro[4.5]decane in a reaction yield of 80%.

Simple distillation was further performed under reduced pressure of 0.13 kPa (absolute pressure), thereby obtaining 297 g of a colorless liquid which was distilled out at a fraction temperature of 123 to 126° C. The purity was 97.0%, and the distillation yield was 95%.

<Spectral Data>

$^1$H-NMR (400 MHz, CDCl$_3$, $\delta_{ppm}$): 1.37-1.42 (2H, m), 1.54-1.63 (8H, m), 2.30 (1H, s), 3.56-3.61 (1H, m), 3.70-3.80 (2H, m), 4.02-4.05 (1H, m), 4.21-4.25 (1H, m)

$^{13}$C-NMR (100 MHz, CDCl$_3$, $\delta_{ppm}$): 23.7, 24.0, 25.1, 34.7, 36.3, 63.1, 65.3, 75.7, 110.0

IR (neat, cm$^{-1}$): 3423 (br), 2933, 2860, 1448, 1365, 1281, 1163, 1097, 1039, 926

MS (m/z): 172 (M$^+$), 143, 129, 116, 81, 73, 55, 41, 31

Production Example 1-4: Production of 2-ethyl-4-hydroxymethyl-2-pentyl-1,3-dioxolane ($R^1$=Et, $R^2$=Pentyl) as a raw material Using 288 g of 3-octanone (purity: 98.0%, 2.20 mol) as a reaction raw material, the same operations as in Production Example 1-1 were followed, thereby obtaining a cis- and trans-isomer mixture of 2-ethyl-4-hydroxymethyl-2-pentyl-1,3-dioxolane in a reaction yield of 73%.

Simple distillation was further performed under reduced pressure of 0.13 kPa (absolute pressure), thereby obtaining 284 g of a stereoisomer mixture which was distilled out as a colorless liquid at a fraction temperature of 143 to 146° C. The purity was 97.4%, and the distillation yield was 85%.
<Spectral Data of Stereoisomer Mixture>
IR (neat, cm$^{-1}$): 3450 (br), 2933, 2871, 1963, 1464, 1165, 1047, 912
MS (m/z, common to two peaks on GC): 202 (M$^+$), 173, 131, 99, 71, 57, 43

Examples: Production of (2,2-dialkyl-1,3-dioxolan-4-yl)methyl 2,2-dialkyl-1,3-dioxolane-4-carboxylate The reaction which was performed in the Examples is as follows.

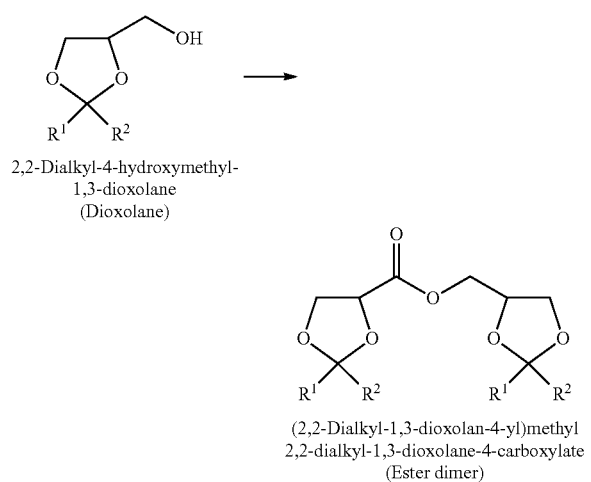

2,2-Dialkyl-4-hydroxymethyl-1,3-dioxolane
(Dioxolane)

(2,2-Dialkyl-1,3-dioxolan-4-yl)methyl 2,2-dialkyl-1,3-dioxolane-4-carboxylate
(Ester dimer)

Example 1-1: Production of (2-ethyl-2-methyl-1,3-dioxolan-4-yl)methyl 2-ethyl-2-methyl-1,3-dioxolane-4-carboxylate ($R^1$=Me, $R^2$=Et)

Example 1-1-1

In a 300-mL flask equipped with a 100-mL dropping funnel, 23.0 g of 2-ethyl-4-hydroxymethyl-2-methyl-1,3-dioxolane (purity 95.3%, 150 mmol) obtained in Production Example 1-1, 23.4 mg of 2-hydroxy-2-azaadamantane (AZADOL, a trademark, manufactured by Nissan Chemical Corporation, purity: 98.0%, 150 µmol), 17.9 g of pyridine (purity: 99.5%, 225 mmol), and 50 g of acetonitrile were charged and stirred in a nitrogen atmosphere while cooling. A solution of 14.7 g of trichloroisocyanuric acid (TCCA, purity: 95.0%, 60 mmol) dissolved in 50 g of acetonitrile was charged in the dropping funnel and dropped over 2 hours while regulating a dropping rate such that the reaction solution temperature within the flask fell within a range of from −2° C. to 10° C. The cooling was stopped, and the stirring was further continued for 3 hours while raising the reaction solution temperature to around 20° C. Finally, 1.81 g of 2-propanol (purity: 99.7%, 30.0 mmol) was added, and the stirring was further performed for 20 minutes, thereby completing the reaction. After filtering off a by-produced powdered solid, the filtrate was subjected to GC analysis. As a result, the conversion of 2-ethyl-4-hydroxymethyl-2-methyl-1,3-dioxolane was 100%, and the yield of (2-ethyl-2-methyl-1,3-dioxolan-4-yl)methyl 2-ethyl-2-methyl-1,3-dioxolane-4-carboxylate was 74%.

In order to remove the powdered solid deposited after distilling off the acetonitrile from the filtrate, 100 g of tert-butylmethyl ether and 50 g of ion exchanged water were added to perform extraction. After settled separation, the lower-layer water was taken out, and 50 g of ion exchanged water was again added, thereby repeating the operation of from extraction to taking-out of the lower-layer water. The resulting organic layer was dried over 20 g of anhydrous sodium sulfate, and after filtration, the tert-butylmethyl ether was distilled out, thereby obtaining 19.8 g of a red oily crude product. As a result of GC analysis of the crude product, the yield of (2-ethyl-2-methyl-1,3-dioxolan-4-yl)methyl 2-ethyl-2-methyl-1,3-dioxolane-4-carboxylate was 72%, and the recovery before and after water washing was 97%.

Subsequently, 17.0 g of the crude product was transferred into a 50-mL flask equipped with a Claisen head, and simple distillation was performed under reduced pressure of 0.13 kPa (absolute pressure), thereby obtaining 11.6 g of (2-ethyl-2-methyl-1,3-dioxolan-4-yl)methyl 2-ethyl-2-methyl-1,3-dioxolane-4-carboxylate which was distilled out as a pale yellow liquid at a fraction temperature of 119 to 122° C. The purity was 98.1%, and the distillation yield was 80%. According to the GC-MS analysis, this ester dimer was confirmed to be a stereoisomer mixture of six kinds composed of at least three pairs of racemates. With respect to other two pairs of racemates, it is estimated that the peaks were overlapped, so that the detection could not be performed.
<Spectral Data of Stereoisomer Mixture>
IR (neat, cm$^{-1}$): 2979, 2939, 2883, 1761, 1736, 1377, 1186, 1072, 874
MS (m/z, common to three peaks on GC): 287, 273, 259, 115, 57, 43

Example 1-1-2

In a 50-mL flask equipped with a 20-mL dropping funnel, 4.60 g of 2-ethyl-4-hydroxymethyl-2-methyl-1,3-dioxolane (purity 95.3%, 30.0 mmol) obtained in Production Example 1-1, 4.7 mg of AZADOL (purity: 98.0%, 30 µmop, 4.92 g of 3,5-lutidine (purity: 98.0%, 45.0 mmol), and 10 g of acetonitrile were charged and stirred in a nitrogen atmosphere while cooling. A solution of 2.94 g of TCCA (purity: 95.0%, 12.0 mmol) dissolved in 10 g of acetonitrile was charged in the dropping funnel and dropped over 1 hour while regulating a dropping rate such that the reaction solution temperature within the flask fell within a range of from −10° C. to 10° C. The cooling was stopped, and the stirring was further continued for 1 hour while raising the reaction solution temperature to around 25° C. Finally, 0.20 g of 2-propanol (purity: 99.7%, 3.3 mmol) was added, and the stirring was further performed for 10 minutes, thereby completing the reaction. After filtering off a by-produced powdered solid, the filtrate was subjected to GC analysis. As a result, the conversion of 2-ethyl-4-hydroxymethyl-2-methyl-1,3-dioxolane was 100%, and the yield of (2-ethyl-2-methyl-1,3-dioxolan-4-yl)methyl 2-ethyl-2-methyl-1,3-dioxolane-4-carboxylate was 73%.

Example 1-2: Production of (2-isobutyl-2-methyl-1,3-dioxolan-4-yl)methyl 2-isobutyl-2-methyl-1,3-dioxolane-4-carboxylate ($R^1$=Me, $R^2$=$^i$Bu)

Using, as a reaction raw material, 26.8 g of 2-isobutyl-4-hydroxymethyl-2-methyl-1,3-dioxolane (purity: 97.4%, 150 mmol) obtained in Production Example 1-2, the same operations as in Example 1-1-1 were performed. As a result of GC analysis of the filtrate, the conversion of 2-isobutyl-4-hydroxymethyl-2-methyl-1,3-dioxolane was 100%, and the yield of (2-isobutyl-2-methyl-1,3-dioxolan-4-yl)methyl 2-isobutyl-2-methyl-1,3-dioxolane-4-carboxylate was 75%. The yield determined by GC analysis of 25.9 g of a dark brown oily crude product was 75%, too, and it was noted that there was no yield loss from the time of analysis of the filtrate.

Subsequently, 20.0 g of the crude product was subjected to simple distillation under reduced pressure of 40 Pa (absolute pressure), thereby obtaining 10.6 g of (2-isobutyl-2-methyl-1,3-dioxolan-4-yl)methyl 2-isobutyl-2-methyl-1,3-dioxolane-4-carboxylate which was distilled out as a yellow liquid at a fraction temperature of 116 to 124° C. The purity was 98.9%, and the distillation yield was 70%. According to the GC-MS analysis, this ester dimer was found to be a stereoisomer mixture of 16 kinds composed of eight pairs of racemates.

<Spectral Data of Stereoisomer Mixture>

IR (neat, cm$^{-1}$): 2933, 2871, 1763, 1736, 1468, 1377, 1182, 1099

MS (m/z, common to eight peaks on GC): 343, 329, 287, 187, 143, 115, 85, 57, 43

Example 1-3: Production of (1,4-dioxaspiro[4.5]decan-2-yl)methyl 1,4-dioxaspiro[4.5]decane-2-carboxylate ($R^1$ and $R^2$=—(CH$_2$)$_5$—)

Example 1-3-1

Using, as a reaction raw material, 26.6 g of 2-hydroxymethyl-1,4-dioxaspiro[4.5]decane (purity: 97.0%, 150 mmol) obtained in Production Example 1-3, the same operations as in Example 1-1-1 were performed. As a result of GC analysis of the filtrate, the conversion of 2-hydroxymethyl-1,4-dioxaspiro[4.5]decane was 100%, and the yield of (1,4-dioxaspiro[4.5]decan-2-yl)methyl 1,4-dioxaspiro[4.5]decane-2-carboxylate was 66%. The yield determined by GC analysis of 23.5 g of a dark orange-colored oily crude product was 66%, too, and it was noted that there was no yield loss from the time of analysis of the filtrate.

Subsequently, 6.50 g of the crude product was distilled under reduced pressure of 40 Pa (absolute pressure) with a Kugelrohr distillation apparatus, thereby obtaining 2.89 g of (1,4-dioxaspiro[4.5]decan-2-yl)methyl 1,4-dioxaspiro[4.5]decane-2-carboxylate which was distilled out as an orange-colored liquid at an apparatus temperature of 225 to 240° C. The purity was 95.6%, and the distillation yield was 60%. According to $^{13}$C-NMR analysis, this ester dimer was found to be a stereoisomer mixture of four kinds composed of two pairs of racemates.

<Spectral Data of Stereoisomer Mixture>

IR (neat, cm$^{-1}$): 2933, 2862, 1761, 1738, 1448, 1367, 1161, 1097, 922

MS (m/z): 340 (M$^+$), 311, 297, 242, 199, 141, 127, 55

Examples 1-3-2 and 1-3-3

Using, as a reaction raw material, 5.32 g of 2-hydroxymethyl-1,4-dioxaspiro[4.5]decane (purity: 97.0%, 30.0 mmol) obtained in Production Example 1-3, the same operations as in Example 1-1-2 were performed, except for changing the reaction conditions as shown in Table 1, thereby obtaining a filtrate containing (1,4-dioxaspiro[4.5]decan-2-yl)methyl 1,4-dioxaspiro[4.5]decane-2-carboxylate. The table shows the reaction conditions and results of Examples 1-3-2 and 1-3-3.

Example 1-3-4

In a 50-mL flask equipped with a dropping funnel, 888 mg of 2-hydroxymethyl-1,4-dioxaspiro[4.5]decane (purity: 97.0%, 5.00 mmol) obtained in Production Example 1-3, 3.95 g of 4-acetamido-2,2,6,6-tetramethyl-1-oxopiperidinum tetrafluoroborate (purity: 95.0%, 12.5 mmol), 1.0 g of molecular sieve 4A which had been previously dried under vacuum heating conditions, and 10 g of dichloromethane were charged and stirred at room temperature in a nitrogen atmosphere. A solution composed of 0.914 g of pyridine (purity: 99.5%, 11.5 mmol) and 5 g of dichloromethane was charged in the dropping funnel and dropped over 20 minutes. Furthermore, after continuing the stirring at room temperature for 3 hours, 0.10 g of methanol (purity: 99.8%, 3.1 mmol) was finally added, and the stirring was further performed for 10 minutes, thereby completing the reaction. After separating the molecular sieve 4A and a by-produced powdered solid through filtration, the filtrate was subjected to GC analysis. As a result, the conversion of 2-hydroxymethyl-1,4-dioxaspiro[4.5]decane was 100%, and the yield of (1,4-dioxospiro[4.5]decan-2-yl)methyl 1,4-dioxaspiro[4.5]decane-2-carboxylate was 64%.

Example 1-4: Production of (2-ethyl-2-pentyl-1,3-dioxolan-4-yl)methyl 2-ethyl-2-pentyl-1,3-dioxolane-4-carboxylate ($R^1$=Et, $R^2$=Pentyl)

Using, as a reaction raw material, 31.2 g of 2-ethyl-4-hydroxymethyl-2-pentyl-1,3-dioxolane (purity: 97.4%, 150 mmol) obtained in Production Example 1-4, the same operations as in Example 1-1-1 were performed. As a result of GC analysis of the filtrate, the conversion of 2-ethyl-4-hydroxymethyl-2-pentyl-1,3-dioxolane was 100%, and the yield of (2-ethyl-2-pentyl-1,3-dioxolan-4-yl)methyl 2-ethyl-2-pentyl-1,3-dioxolane-4-carboxylate was 73%. The yield determined by GC analysis of 33.0 g of a dark brown oily crude product was 70%, and it was noted that there was a yield loss of 3% from the time of analysis of the filtrate.

Subsequently, 6.05 g of the crude product was distilled under reduced pressure of 40 Pa (absolute pressure) with a Kugelrohr distillation apparatus, thereby obtaining 2.03 g of (2-ethyl-2-pentyl-1,3-dioxolan-4-yl)methyl 2-ethyl-2-pentyl-1,3-dioxolane-4-carboxylate which was distilled out as an orange-colored liquid at an apparatus temperature of 180 to 210° C. The purity was 90.6%, and the distillation yield was 48%. According to GC-MS analysis, this ester dimer was found to be a stereoisomer mixture of 16 kinds composed of eight pairs of racemates.

<Spectral Data of Stereoisomer Mixture>

IR (neat, cm$^{-1}$): 2931, 2875, 1763, 1736, 1466, 1190, 1165, 1105, 908

MS (m/z, common to eight peaks on GC): 400 (M$^+$), 371, 329, 171, 129, 99, 71, 57, 43

Comparative Example 1-1: Production of (2,2-dimethyl-1,3-dioxolan-4-yl)methyl 2,2-dimethyl-1,3-dioxolane-4-carboxylate ($R^1$ and $R^2$=Me)

Using, as a reaction raw material, 20.2 g of 2,2-dimethyl-4-hydroxymethyl-1,3-dioxolane (a trade name: 2,2-dimethyl-1,3-dioxolane-4-metanol, manufactured by Tokyo Chemical Industry Co., Ltd., purity: 98.0%, 150 mmol), the same operations as in Example 1-1-1 were performed. As a result of GC analysis of the filtrate, the conversion of 2,2-dimethyl-4-hydroxymethyl-1,3-dioxolane was 100%, and the yield of (2,2-dimethyl-1,3-dioxolan-4-yl)methyl 2,2-dimethyl-1,3-dioxolane-4-carboxylate was 70%. The yield determined by GC analysis of 15.1 g of a dark orange-colored oily crude product was 59%, and it was noted that there was a yield loss of 11% from the time of analysis of the filtrate.

Subsequently, 14.1 g of the crude product was subjected to simple distillation under reduced pressure of 0.13 kPa (absolute pressure), thereby obtaining 8.20 g of (2,2-dimethyl-1,3-dioxolan-4-yl)methyl 2,2-dimethyl-1,3-dioxolane-4-carboxylate which was distilled out as a colorless liquid at a fraction temperature of 103 to 106° C. The purity was 98.7%, and the distillation yield was 97%. According to the $^{13}$C-NMR analysis, this ester dimer was found to be a stereoisomer mixture of four kinds composed of two pairs of racemates.

<Spectral Data of Stereoisomer Mixture>

IR (neat, cm$^{-1}$): 2987, 2939, 1759, 1734, 1371, 1192, 1153, 1099, 1066, 837

MS (m/z): 259, 245, 186, 130, 115, 101, 73, 59, 43

The reaction conditions and results of Examples 1-1 to 1-4 and Comparative Example 1-1 are shown in the following table.

TABLE 1

| Example | $R^1$, $R^2$ | Catalyst Name | Catalyst Molar ratio[1] | Oxidizing agent Name | Oxidizing agent Molar ratio[1] | Base Name | Base Molar ratio[1] | Solvent |
|---|---|---|---|---|---|---|---|---|
| 1-1-1 | Me, Et | AZADOL | 0.001 | TCCA | 0.40 | Pyridine | 1.5 | Acetonitrile |
| 1-1-2 | Me, Et | AZADOL | 0.010 | TCCA | 0.40 | 3,5-Lutidine | 1.5 | Acetonitrile |
| 1-2 | Me, $^i$Bu | AZADOL | 0.001 | TCCA | 0.40 | Pyridine | 1.5 | Acetonitrile |
| 1-3-1 | —(CH$_2$)$_5$— | AZADOL | 0.001 | TCCA | 0.40 | Pyridine | 1.5 | Acetonitrile |
| 1-3-2 | —(CH$_2$)$_5$— | AZADOL | 0.010 | TCCA | 0.35 | Pyridine | 2.0 | Acetonitrile |
| 1-3-3 | —(CH$_2$)$_5$— | AZADOL | 0.010 | $^t$BuOCl | 2.0 | Pyridine | 2.0 | Acetonitrile |
| 1-3-4 | —(CH$_2$)$_5$— | 4-NHAc-TEMPO salt[3] | 2.5 | None | — | Pyridine | 2.0 | Dichloromethane |
| 1-4 | Et, Pentyl | AZADOL | 0.001 | TCCA | 0.40 | Pyridine | 1.5 | Acetonitrile |
| Comparative Example 1-1 | Me, Me | AZADOL | 0.001 | TCCA | 0.40 | Pyridine | 1.5 | Acetonitrile |

| Example | Reaction time (hr)[2] | Conversion of dioxolane (%) | Yield of ester dimer (%) Filtrate | Yield of ester dimer (%) Crude product | Yield of ester dimer (%) Recovery before and after water washing |
|---|---|---|---|---|---|
| 1-1-1 | 5 | 100 | 74 | 72 | 97 |
| 1-1-2 | 2 | 100 | 73 | Not analyzed | Not analyzed |
| 1-2 | 5 | 100 | 75 | 75 | 100 |
| 1-3-1 | 5 | 100 | 66 | 66 | 100 |
| 1-3-2 | 4 | 100 | 84 | Not analyzed | Not analyzed |
| 1-3-3 | 3 | 100 | 81 | Not analyzed | Not analyzed |
| 1-3-4 | 3.5 | 100 | 64 | Not analyzed | Not analyzed |
| 1-4 | 5 | 100 | 73 | 70 | 96 |
| Comparative Example 1-1 | 5 | 100 | 70 | 59 | 84 |

[1] Molar ratio to dioxolane
[2] Time from start of dropping to completion of reaction
[3] 4-Acetamido-2,2,6,6-tetramethyl-1-oxopiperidinum tetrafluoroborate Example 1-5: Production of Ethyl Glycerate The reaction which was performed in Example 1-5 is as follows.

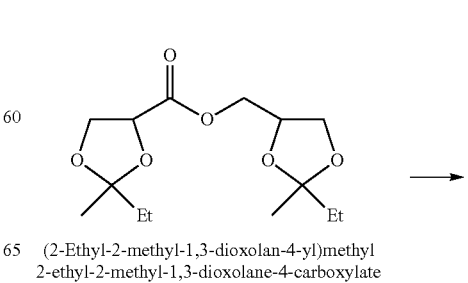

(2-Ethyl-2-methyl-1,3-dioxolan-4-yl)methyl 2-ethyl-2-methyl-1,3-dioxolane-4-carboxylate -continued

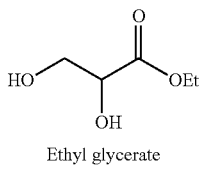
Ethyl glycerate

In a 100-mL flask, 5.00 g of (2-ethyl-2-methyl-1,3-dioxolan-4-yl)methyl 2-ethyl-2-methyl-1,3-dioxolane-4-carboxylate (purity: 98.1%, 17.0 mmol) obtained in Example 1-1-1, 83 mg of methanesulfonic acid (purity: 98.0%, 0.85 mmol), and 39.4 g of ethanol (purity: 99.5%, 850 mmol) were charged and refluxed for 2 hours. After cooling, the resultant was neutralized with 290 mg of a 20% ethanol solution of sodium ethoxide (58 mg, 0.85 mmol as sodium ethoxide), and the ethanol was distilled off. Subsequently, 8.75 g of the resulting orange-colored oily crude product was purified with a Kugelrohr distillation apparatus. There was thus obtained 1.53 g of ethyl glycerate which was distilled out as a colorless liquid under conditions at 0.13 kPa (absolute pressure) and at an apparatus temperature of 150 to 155° C. The purity was 93.5%, and the yield was 63%.

<Spectral Data of Ethyl Glycerate>

$^1$H-NMR (400 MHz, CDCl$_3$, $\delta_{ppm}$): 1.31 (3H, t, J=6.8 Hz), 3.82-3.92 (2H, m), 4.24-4.30 (3H, m); the $^1$H peak of the hydroxy group became broad, so that it could not be detected.

$^{13}$C-NMR (100 MHz, CDCl$_3$, $\delta_{ppm}$): 14.1, 62.0, 64.1, 71.8, 173.0

IR (neat, cm$^{-1}$): 3425 (br), 2974, 2935, 1728, 1201, 1111, 1063, 1020

MS (m/z): 134 (M$^+$), 104, 76, 61, 43, 31

Production Example 2-1: Production of a Mixture of 2-phenyl-1,3-dioxan-5-ol and 4-hydroxymethyl-2-phenyl-1,3-dioxolane as a Raw Material The reaction which was performed in Production Example 2-1 is as follows.

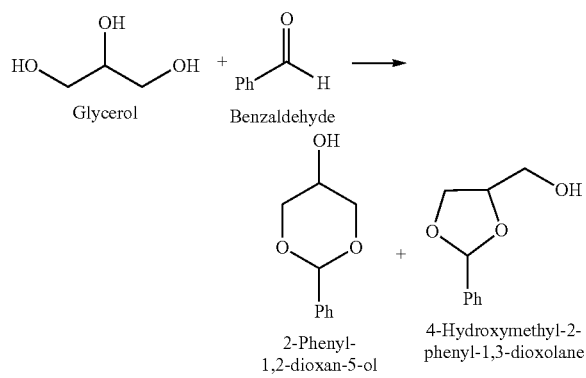

In a one-liter flask equipped with a Dean-Stark apparatus, 184 g of glycerol (purity: 100%, 2.00 mol), 238 g of benzaldehyde (purity: 98.0%, 2.20 mol), 18 g of AMBERLYST 15DRY (strongly acidic cation exchange resin, manufactured by The Dow Chemical Company, a trademark), and 50 g of n-hexane were charged and refluxed for 6 hours while removing water by-produced by the reaction outside the reaction system. After cooling, the ion exchange resin was filtered off, and the filtrate was subjected to GC analysis. As a result, a reaction yield of an isomer mixture of four kinds composed of cis- and trans-2-phenyl-1,3-dioxan-5-ol and cis- and trans-4-hydroxymethyl-2-phenyl-1,3-dioxolane was 91%.

Subsequently, the filtrate was transferred into a 500-mL flask equipped with a Claisen head; after heating at 50° C., the pressure was gradually reduced to distill off the n-hexane; and simple distillation was further performed under reduced pressure of 0.13 kPa (absolute pressure), thereby obtaining 317 g of an isomer mixture which was distilled out as a colorless liquid at a fraction temperature of 110 to 120° C. The purity was 100%, and the distillation yield was 97%.

Reference Literature 1 (Journal of Catalysis, Vol. 245, pp. 428-435, 2007) describes $^1$H-NMR signal assignment of a proton at the 2-position of each isomer. An isomer ratio of 2-phenyl-1,3-dioxan-5-ol to 4-hydroxymethyl-2-phenyl-1,3-dioxolane determined from this information and the $^1$H-NMR analysis was 49/51.

<Spectral Data of Isomer Mixture>

IR (neat, cm$^{-1}$): 3429 (br), 2991, 2937, 2856, 1408, 1151, 1082, 1039

Production Example 2-2: Production of a Mixture of 2-phenyl-1,3-dioxan-5-ol and 4-hydroxymethyl-2-phenyl-1,3-dioxolane as a Raw Material The reaction which was performed in Production Example 2-2 is as follows.

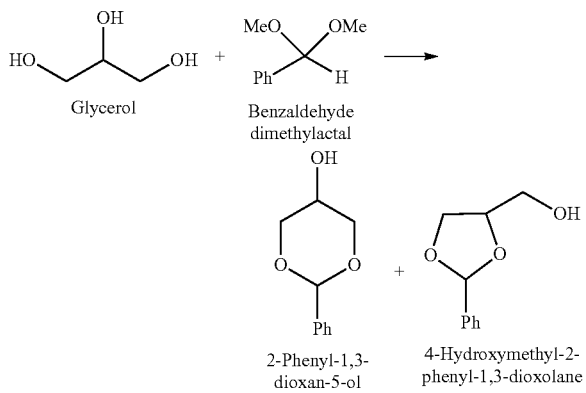

In a 100-mL flask, 9.21 g of glycerol (purity: 100%, 100 mmol), 17.1 g of benzaldehyde dimethylacetal (purity: 98.0%, 110 mmol), 0.50 g of AMBERLYST 36 (strongly acidic cation exchange resin, manufactured by The Dow Chemical Company, a trademark), and 23 g of dichloromethane were charged and stirred at 25° C. for 6 hours in a nitrogen atmosphere. The ion exchange resin was filtered off, and the dichloromethane was distilled off from the filtrate, followed by performing GC analysis. As a result, a reaction yield of an isomer mixture of four kinds composed of cis- and trans-2-phenyl-1,3-dioxan-5-ol and cis- and trans-4-hydroxymethyl-2-phenyl-1,3-dioxolane was 77%. In addition, an isomer ratio of 2-phenyl-1,3-dioxan-5-ol to 4-hydroxymethyl-2-phenyl-1,3-dioxolane determined from the information of Reference Literature 1 and the $^1$H-NMR analysis was 55/45.

Production Example 2-3: Production of a Mixture of 2-methyl-1,3-dioxan-5-ol and 4-hydroxymethyl-2-methyl-1,3-dioxolane as a Raw Material The reaction which was performed in Production Example 2-3 is as follows.

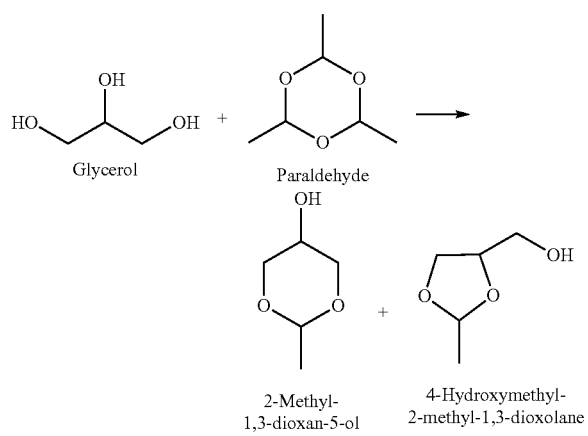

Glycerol + Paraldehyde → 2-Methyl-1,3-dioxan-5-ol + 4-Hydroxymethyl-2-methyl-1,3-dioxolane In a 500-mL flask equipped with a Dean-Stark apparatus, 184 g of glycerol (purity: 100%, 2.00 mol), 117 g of paraldehyde (purity: 98.0%, 868 mmol), 981 mg of methanesulfonic acid (purity: 98.0%, 10.0 mmol), and 40 g of n-hexane were charged and refluxed for 5 hours while removing water by-produced by the reaction outside the reaction system. After cooling, the reaction solution was neutralized with 3.50 g of a 20% ethanol solution of sodium ethoxide (700 mg as sodium ethoxide, 10.3 mmol). As a result of analyzing the reaction solution, a reaction yield of an isomer mixture of four kinds composed of cis- and trans-2-methyl-1,3-dioxan-5-ol and cis- and trans-4-hydroxymethyl-2-methyl-1,3-dioxolane was 71%.

Subsequently, the reaction solution was transferred into a 500-mL flask equipped with a Claisen head; after heating at 50° C., the pressure was gradually reduced to distill off the n-hexane and the ethanol; and simple distillation was further performed under reduced pressure of 0.67 kPa (absolute pressure), thereby obtaining 160 g of an isomer mixture composed of four kinds of cis- and trans-2-methyl-1,3-dioxan-5-ol and cis- and trans-4-hydroxymethyl-2-methyl-1,3-dioxolane, which was distilled out as a colorless liquid at a fraction temperature of 62 to 70° C. The purity was 100%, and the distillation yield was 96%.

Reference Literature 2 (Tetrahedron, Vol. 71, No. 20, pp. 3032-3038, 2015) describes $^1$H-NMR signal assignment of a proton at the 2-position of each isomer. An isomer ratio of 2-methyl-1,3-dioxan-5-ol to 4-hydroxymethyl-2-methyl-1, 3-dioxolane determined from the information and the $^1$H-NMR analysis was 70/30.

<Spectral Data of Isomer Mixture>

IR (neat, cm$^{-1}$): 3415 (br), 2856, 1456, 1394, 1149, 1086

Production Example 2-4: Production of a Mixture of 2-n-heptyl-1,3-dioxan-5-ol and 4-Hydroxymethyl-2-n-heptyl-1,3-dioxolane as a Raw Material The reaction which was performed in Production Example 2-4 is as follows.

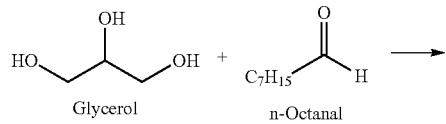

Glycerol + n-Octanal →

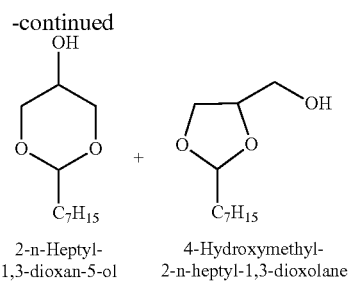

2-n-Heptyl-1,3-dioxan-5-ol + 4-Hydroxymethyl-2-n-heptyl-1,3-dioxolane

In a 300-mL flask equipped with a Dean-Stark apparatus, 69.1 g of glycerol (purity: 100%, 750 mmol), 98.1 g of n-octanal (purity: 98.0%, 750 mmol), 368 mg of methanesulfonic acid (purity: 98.0%, 3.75 mmol), and 18 g of n-hexane were charged and refluxed for 3 hours while removing water by-produced by the reaction outside the reaction system. After cooling, the reaction solution was neutralized with 1.30 g of a 20% ethanol solution of sodium ethoxide (260 mg as sodium ethoxide, 3.82 mmol). As a result of analyzing the reaction solution, a reaction yield of an isomer mixture of four kinds composed of cis- and trans-2-n-heptyl-1,3-dioxan-5-ol and cis- and trans-4-hydroxymethyl-2-n-heptyl-1,3-dioxolane was 100%.

Subsequently, the reaction solution was transferred into a 200-mL flask equipped with a Claisen head; after heating at 50° C., the pressure was gradually reduced to distill off the n-hexane and the ethanol; and simple distillation was further performed under reduced pressure of 67 kPa (absolute pressure), thereby obtaining 135 g of an isomer mixture composed of four kinds of cis- and trans-2-n-heptyl-1,3-dioxan-5-ol and cis- and trans-4-hydroxymethyl-2-n-heptyl-1,3-dioxolane, which was distilled out as a colorless liquid at a fraction temperature of 95 to 102° C. The purity was 99%, and the distillation yield was 89%.

Reference Literature 3 (Green Chemistry, Vol. 12, pp. 2225-2231, 2010) describes $^1$H-NMR signal assignment of a proton at the 2-position of each isomer. An isomer ratio of 2-heptyl-1,3-dioxan-5-ol to 4-hydroxymethyl-2-heptyl-1,3-dioxolane determined from the information and the $^1$H-NMR analysis was 57/43.

<Spectral Data of Isomer Mixture>

IR (neat, cm$^{-1}$): 3479 (br), 2954, 2854, 1462, 1394, 1146, 1043

Example 2-1: Production of (1,3-Dioxolan-4-yl)methyl 1,3-dioxolane-4-carboxylate The reaction which was performed in Example 2-1 is as follows.

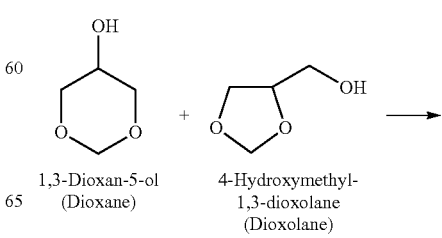

1,3-Dioxan-5-ol (Dioxane) + 4-Hydroxymethyl-1,3-dioxolane (Dioxolane) →

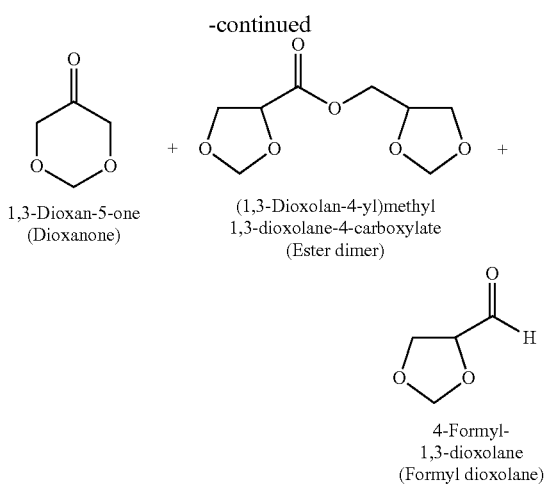

1,3-Dioxan-5-one (Dioxanone)

(1,3-Dioxolan-4-yl)methyl 1,3-dioxolane-4-carboxylate (Ester dimer)

4-Formyl-1,3-dioxolane (Formyl dioxolane)

Example 1-1

In a one-liter flask equipped with a 100-mL dropping funnel, 63.7 g of a mixture of 1,3-dioxan-5-ol and 4-hydroxymethyl-1,3-dioxolane (a trade name: Glycerol Formal, manufactured by Tokyo Chemical Industry Co., Ltd., purity: 98.0%, 600 mmol, an isomer ratio of 1,3-dioxan-5-ol to 4-hydroxymethyl-1,3-dioxolane determined from the information of Reference Literature 1 and the $^1$H-NMR analysis: 58/42), 93.8 mg of 2-hydroxy-2-azaadamantane (AZADOL, a trademark, manufactured by Nissan Chemical Corporation, purity: 98.0%, 0.60 mmol), 71.5 g of pyridine (purity: 99.5%, 900 mmol), and 150 g of acetonitrile were charged and stirred in a nitrogen atmosphere while cooling. A solution of 58.7 g of trichloroisocyanuric acid (TCCA, purity: 95.0%, 240 mmol) dissolved in 150 g of acetonitrile was charged three separate times in the dropping funnel and dropped over 3.5 hours while regulating a dropping rate such that the reaction solution temperature within the flask fell within a range of from −2° C. to 2° C. The cooling was stopped, and the stirring was further continued for 4 hours while raising the reaction solution temperature to around 20° C. Finally, 7.23 g (purity: 99.7%, 120 mmol) of 2-propanol was added, and the stirring was further performed for 20 minutes, thereby completing the reaction. After filtering off a by-produced powdered solid, 100 g of tert-butyl methyl ether was added to the reaction solution from which the acetonitrile had been distilled off, and the filtration-off of the deposited powdered solution and the distillation-off of the solvent were repeated two times, thereby obtaining 70.5 g of an orange-colored oily crude product. As a result of GC analysis of the crude product, the conversion of 4-hydroxymethyl-1,3-dioxolane was 100%, and the yield of (1,3-dioxolan-4-yl)methyl 1,3-dioxolane-4-caboxylate was 95%.

In a 200-mL pear shape flask equipped with a packed distillation tower having the number of theoretical stages of 6 (packing: Helipack packing No. 2), 65.0 g of the crude product was charged, and 21.9 g of (1,3-dioxolan-4-yl)methyl 1,3-dioxolane-4-caboxylate which was distilled out as a pale yellow liquid at a fraction temperature of 89 to 91° C. under conditions at 0.13 kPa (absolute pressure) and at a reflux ratio of 0.1 The purity was 98.8%, and the distillation yield was 96%. $^{13}$C-NMR analysis suggested that this ester dimer was a stereoisomer mixture of four kinds composed of two pairs of racemates.

FIG. 1 is a GC chart of the reaction solution obtained in Example 2-1-1.

Spectral Data of (1,3-Dioxolan-4-yl)methyl 1,3-dioxolane-4-caboxylate (Stereoisomer Mixture)

IR (neat, cm$^{-1}$): 2956, 2856, 1751, 1284, 1151, 1082, 1016, 916
MS (m/z): 204 (M$^+$), 159, 129, 86, 73, 57, 45

Example 2-1-2

In a 50-mL flask equipped with a 20-mL dropping funnel, 3.19 g of the same Glycerol Formal as in Example 2-1-1 (purity: 98.0%, 30.0 mmol), 4.7 mg of AZADOL (purity: 98.0%, 30 μmop, 4.77 g of pyridine (purity: 99.5%, 60.0 mmol), and 10 g of acetonitrile were charged and stirred in a nitrogen atmosphere while cooling. A solution of 2.94 g of TCCA (purity: 95.0%, 12.0 mmol) dissolved in 10 g of acetonitrile was charged in the dropping funnel and dropped over 1 hour while regulating a dropping rate such that the reaction solution temperature within the flask fell within a range of from −10° C. to 10° C. The cooling was stopped, and the stirring was further continued for 2 hours while raising the reaction solution temperature to around 25° C. Finally, 0.20 g (purity: 99.7%, 3.3 mmol) of 2-propanol was added, and the stirring was further performed for 10 minutes, thereby completing the reaction. After filtering off a by-produced powdered solid, the filtrate was subjected to GC analysis. As a result, the conversion of the conversion of 4-hydroxymethyl-1,3-dioxolane was 100%, and the yield of (1,3-dioxolan-4-yl)methyl 1,3-dioxolane-4-caboxylate was 99%.

Examples 2-1-3 to 2-1-11

The same operations as in Example 2-1-2 were followed, except for changing the kind or use amount of the catalyst, the kind or use amount of the base, or the solvent species. The reaction conditions and results of Examples 2-1-2 to 2-1-11 are shown in Table 2.

TABLE 2

| | Catalyst | | Oxidizing agent | | Base | | | Reaction | Conversion | Yield of |
|---|---|---|---|---|---|---|---|---|---|---|
| Example | Name | Molar ratio [1] | Name | Molar ratio [1] | Name | Molar ratio [1] | Solvent | time (hr) [2] | of dioxolane (%) | ester dimer (%) |
| 2-1-2 | AZADOL | 0.001 | TCCA | 0.40 | Pyridine | 2.0 | Acetonitrile | 3 | 100 | 99 |
| 2-1-3 | AZADOL | 0.001 | TCCA | 0.40 | Pyridine | 1.1 | Acetonitrile | 4 | 100 | 100 |
| 2-1-4 | AZADOL | 0.001 | TCCA | 0.40 | 3,5-Lutidine | 1.5 | Acetonitrile | 2 | 100 | 94 |
| 2-1-5 | AZADOL | 0.001 | TCCA | 0.40 | 3-Ethylpyridine | 1.5 | Acetonitrile | 3 | 100 | 93 |
| 2-1-6 | AZADOL | 0.001 | TCCA | 0.40 | 3,5-Lutidine | 1.5 | 2-Butanone | 2 | 100 | 91 |
| 2-1-7 | AZADOL | 0.001 | TCCA | 0.40 | Pyridine | 1.5 | Cyclopentanone | 2 | 100 | 97 |
| 2-1-8 | TEMPO | 0.010 | TCCA | 0.40 | 3,5-Lutidine | 1.5 | Acetonitrile | 6 | 100 | 100 |

TABLE 2-continued

| Example | Catalyst Name | Molar ratio [1] | Oxidizing agent Name | Molar ratio [1] | Base Name | Molar ratio [1] | Solvent | Reaction time (hr) [2] | Conversion of dioxolane (%) | Yield of ester dimer (%) |
|---|---|---|---|---|---|---|---|---|---|---|
| 2-1-9 | 4-OMe-TEMPO | 0.010 | TCCA | 0.40 | 3,5-Lutidine | 1.5 | Acetonitrile | 3 | 100 | 100 |
| 2-1-10 | 4-OBz-TEMPO | 0.010 | TCCA | 0.40 | 3,5-Lutidine | 1.5 | Acetonitrile | 3 | 100 | 91 |
| 2-1-11 | 4-OMs-TEMPO | 0.005 | TCCA | 0.40 | Pyridine | 1.5 | 2-Butanone | 6 | 100 | 93 |

[1] Molar ratio to the mixture of 1,3-dioxan-5-ol and 4-hydroxymethyl-1,3-dioxolane
[2] Time from start of dropping to completion of reaction

Example 2-2: Production of (2-Phenyl-1,3-dioxolan-4-yl)methyl 2-phenyl-1,3-dioxolane The reaction which was performed in Example 2-2 is as follows.

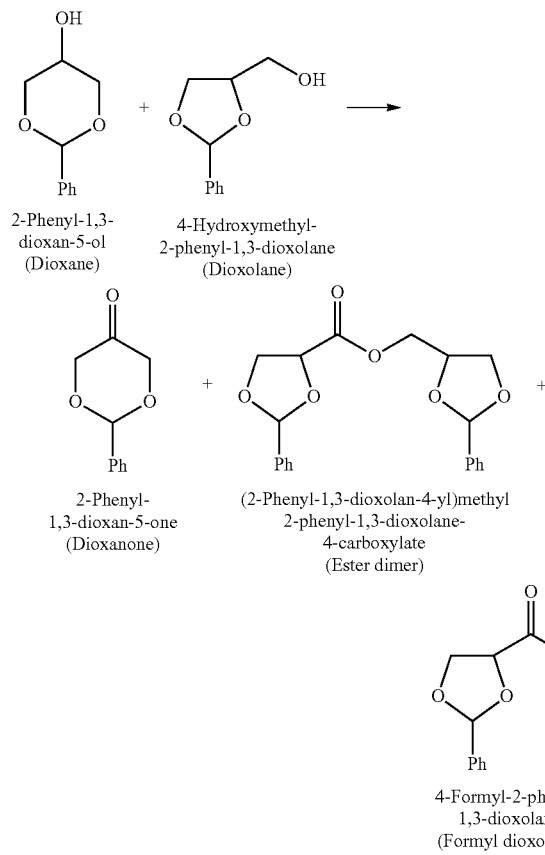

2-Phenyl-1,3-dioxan-5-ol (Dioxane)
4-Hydroxymethyl-2-phenyl-1,3-dioxolane (Dioxolane)
2-Phenyl-1,3-dioxan-5-one (Dioxanone)
(2-Phenyl-1,3-dioxolan-4-yl)methyl 2-phenyl-1,3-dioxolane-4-carboxylate (Ester dimer)
4-Formyl-2-phenyl-1,3-dioxolane (Formyl dioxolane)

Examples 2-2-1 and 2-2-2

Using, as a reaction raw material, 3.60 g (purity: 100%, 20.0 mmol) of the mixture of 2-phenyl-1,3-dioxan-5-ol and 4-hydroxymethyl-2-phenyl-1,3-dioxolane obtained in Production Example 2-1, the same operations as in Example 2-1-2 were followed, thereby obtaining a reaction solution containing of (2-phenyl-1,3-dioxolan-4-yl)methyl 2-phenyl-1,3-dioxolane-4-caboxylate. The reaction conditions and results of Examples 2-2-1 and 2-2-2 are shown in Table 3.

The reaction solutions obtained in Examples 2-2-1 and 2-2-2 were mixed and subjected to simple distillation under reduced pressure of 0.13 kPa (absolute pressure), thereby distilling off low-boiling components, such as 2-phenyl-1,3-dioxan-5-one. Subsequently, a component having an Rf value of 0.24 was separated by silica gel column chromatography of a dark brown oily simple distillation residue (developing solvent: n-hexane/ethyl acetate=3), and after solvent distillation-off and vacuum drying, 2.58 g of orange-colored liquid-like (2-phenyl-1,3-dioxolan-4-yl)methyl 2-phenyl-1,3-dioxolane-4-caboxylate. The purity was 90.6%, and the purification yield was 78%. According to the GC-MS analysis, the ester dimer was confirmed to be a stereoisomer mixture composed of at least six pairs of racemates. With respect to other two pairs of racemates, it is estimated that the peaks were overlapped, so that the detection could not be performed.

FIG. 2 is a GC chart of the reaction solution obtained in Example 2-2-1.

Spectral Data of (2-Phenyl-1,3-dioxolan-4-yl)methyl 2-phenyl-1,3-dioxolane-4-caboxylate (Stereoisomer Mixture)

IR (neat, cm$^{-1}$): 2881, 1751, 1734, 1458, 1394, 1200, 1080, 648

MS (m/z, common to six peaks on GC): 356 (M$^+$), 250, 233, 149, 129, 105, 91, 77, 55

TABLE 3

| Example | Catalyst Name | Molar ratio [1] | Oxidizing agent Name | Molar ratio [1] | Base Name | Molar ratio [1] | Solvent | Reaction time (hr) [2] | Conversion of dioxolane (%) | Yield of ester dimer (%) |
|---|---|---|---|---|---|---|---|---|---|---|
| 2-2-1 | AZADOL | 0.010 | TCCA | 0.40 | Pyridine | 2.0 | Acetonitrile | 2 | 100 | 100 |
| 2-2-2 | AZADOL | 0.010 | $^t$BuOCl | 2.0 | Pyridine | 2.0 | Acetonitrile | 2 | 100 | 82 |

[1] Molar ratio to the mixture of 2-phenyl-1,3-dioxan-5-ol and 4-hydroxymethyl-2-phenyl-1,3-dioxolane
[2] Time from start of dropping to completion of reaction Example 2-3: Production of (2-methyl-1,3-dioxolan-4-yl)methyl 2-methyl-1,3-dioxolane-4-carboxylate The reaction which was performed in Example 2-3 is as follows.

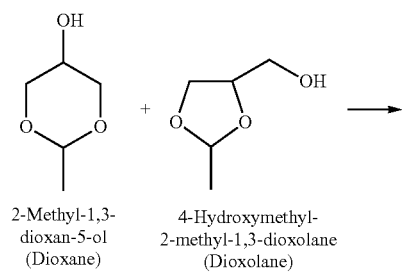

2-Methyl-1,3-dioxan-5-ol
(Dioxane)

4-Hydroxymethyl-2-methyl-1,3-dioxolane
(Dioxolane)

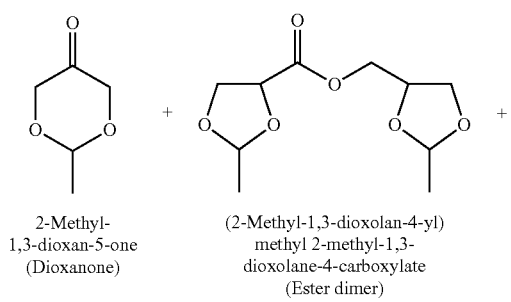

2-Methyl-1,3-dioxan-5-one
(Dioxanone)

(2-Methyl-1,3-dioxolan-4-yl)methyl 2-methyl-1,3-dioxolane-4-carboxylate
(Ester dimer)

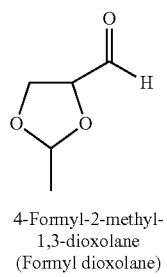

4-Formyl-2-methyl-1,3-dioxolane
(Formyl dioxolane)

oily crude product. As a result of GC analysis of the crude product, the conversion of 2-methyl-4-hydroxymethyl-1,3-dioxolane was 100%, and the yield of (2-methyl-1,3-dioxolan-4-yl)methyl 2-methyl-1,3-dioxolane-4-caboxylate was 88%.

In a 100-mL pear shape flask equipped with a packed distillation tower having the number of theoretical stages of 6 (packing: Helipack packing No. 2), 60.0 g of the crude product was charged, and 16.1 g of (2-methyl-1,3-dioxolan-4-yl)methyl 2-methyl-1,3-dioxolane-4-carboxylate which was distilled out as a pale yellow liquid at a fraction temperature of 110 to 113° C. under conditions at 0.13 kPa (absolute pressure) and at a reflux ratio of 0.5. The purity was 98.6%, and the distillation yield was 95%. According to $^{13}$C-NMR and GC-MS analyses, the ester dimer was confirmed to be a stereoisomer mixture of four kinds composed of at least two pairs of racemates. With respect to other two pairs of racemates, it is estimated that the peaks were overlapped, so that the detection could not be performed.

Spectral Data of (2-Methyl-1,3-dioxolan-4-yl)methyl 2-methyl-1,3-dioxolane-4-caboxylate (Stereoisomer Mixture)

IR (neat, cm$^{-1}$): 2991, 2864, 1751, 1408, 1201, 1146, 1088, 1076, 858

MS (m/z, common to two peaks on GC): 232 (M$^+$), 217, 173, 129, 101, 87, 59, 43

Examples 2-3-2 to 2-3-4

Using, as a reaction raw material, 3.54 g of a mixture of 2-methyl-1,3-dioxan-5-ol and 4-hydroxymethyl-2-methyl-1,3-dioxolane (purity: 100%, 30.0 mmol) obtained in Production Example 2-3, the same operations as in Example 2-1-2 were performed, thereby obtaining a reaction solution containing (2-methyl-1,3-dioxolan-4-yl)methyl 2-methyl-1,3-dioxolane-4-carboxylate. The reaction conditions and results of Examples 2-3-2 to 2-3-4 are shown in Table 4.

FIG. 3 is a GC chart of the reaction solution obtained in Example 2-3-3.

TABLE 4

| | Catalyst | | Oxidizing agent | | Base | | | Reaction | Conversion | Yield of |
|---|---|---|---|---|---|---|---|---|---|---|
| Example | Name | Molar ratio[1] | Name | Molar ratio[1] | Name | Molar ratio[1] | Solvent | time (hr)[2] | of dioxolane (%) | ester dimer (%) |
| 2-3-2 | 4-NHAc-TEMPO | 0.010 | TCCA | 0.40 | 3,5-Lutidine | 1.5 | Acetonitrile | 2 | 100 | 94 |
| 2-3-3 | AZADOL | 0.010 | TCCA | 0.40 | 3,5-Lutidine | 1.3 | Acetonitrile | 2 | 100 | 99 |
| 2-3-4 | 4-OBz-TEMPO | 0.010 | TCCA | 0.40 | 3,5-Lutidine | 1.3 | Acetonitrile | 2 | 100 | 95 |

[1] Molar ratio to the mixture of 2-methyl-1,3-dioxan-5-ol and 4-hydroxymethyl-2-methyl-1,3-dioxolane
[2] Time from start of dropping to completion of reaction Example 2-3-1

Using, as a reaction raw material, 70.9 g (purity: 100%, 600 mmol) of the mixture of 2-methyl-1,3-dioxan-5-ol and 4-hydroxymethyl-2-methyl-1,3-dioxolane obtained in Production Example 2-3, the same operations as in Example 2-1-1 were followed, thereby obtaining 66.2 g of a yellow Example 2-4: Production of (2-n-heptyl-1,3-dioxolan-4-yl)methyl 2-n-heptyl-1,3-dioxolane-4-carboxylate The reaction which was performed in Production Example 2-4 is as follows.

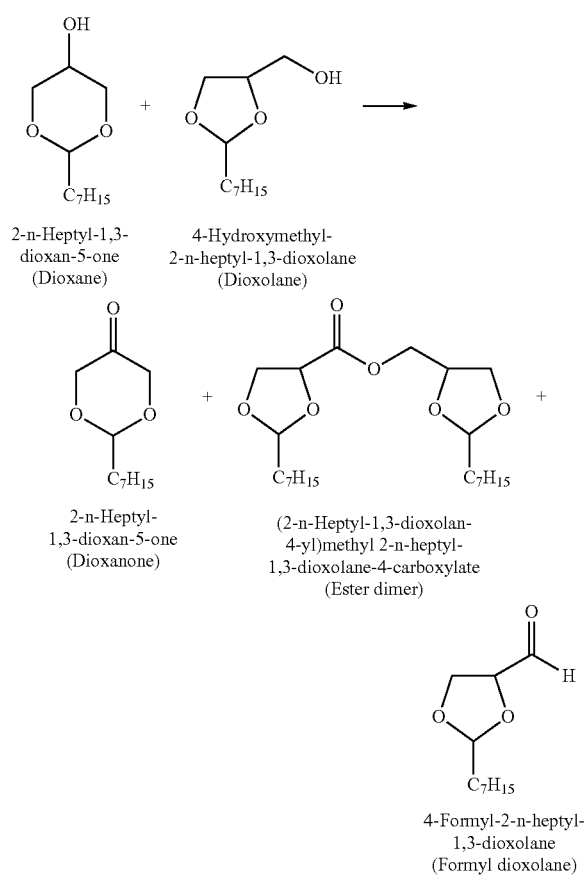

2-n-Heptyl-1,3-dioxan-5-one (Dioxane)

4-Hydroxymethyl-2-n-heptyl-1,3-dioxolane (Dioxolane)

2-n-Heptyl-1,3-dioxan-5-one (Dioxanone)

(2-n-Heptyl-1,3-dioxolan-4-yl)methyl 2-n-heptyl-1,3-dioxolane-4-carboxylate (Ester dimer)

4-Formyl-2-n-heptyl-1,3-dioxolane (Formyl dioxolane)

Using, as a reaction raw material, 4.34 g (purity: 99.2%, 21.3 mmol) of the mixture of 2-n-heptyl-1,3-dioxan-5-ol and 4-hydroxymethyl-2-n-heptyl-1,3-dioxolane obtained in Production Example 2-4, the same reaction operations as in Example 2-1-1 were followed. For the purposes of filtration of a powdered solid and removal of a powdered solid redeposited after distilling off acetonitrile, 20 g of tert-butyl methyl ether and 10 g of ion exchanged water were added, and a saturated sodium hydrogencarbonate aqueous solution was further added until the pH of the aqueous layer became 8, followed by extraction. After static layer separation, the lower layer water was drawn out, 20 g of a saturated sodium chloride aqueous solution was added, and an operation of from extraction to drawing-out of the lower layer water was repeated. The resulting organic layer was dried over 10 g of anhydrous sodium sulfate, and after filtration, the tert-butyl methyl ether was distilled out, thereby obtaining 5.40 g of a pale yellow oily crude product. As a result of GC analysis of the crude product, the conversion of 2-n-heptyl-1,3-dioxan-5-ol was 93%; the yield of 2-n-heptyl-1,3-dioxan-5-one was 74%; the conversion of 2-n-heptyl-4-hydroxymethyl-1,3-dioxolane was 100%; the yield of (2-n-heptyl-1,3-dioxolan-4-yl)methyl 2-n-heptyl-1,3-dioxolane-4-caboxylate was 98%; and the yield of 4-formyl-n-hpetyl-1,3-dioxolane was 2%.

Subsequently, 5.00 g of the crude product was distilled under reduced pressure of 40 Pa (absolute pressure) with a Kugelrohr distillation apparatus, thereby obtaining 1.35 g of 2-n-heptyl-1,3-dioxan-5-one which was distilled out as a colorless liquid at an apparatus temperature of 140 to 160° C. The purity was 97%, and the distillation yield was 78%.

In addition, the purity of (2-n-heptyl-1,3-dioxolan-4-yl)methyl 2-n-heptyl-1,3-dioxolane-4-carboxylate in 1.86 g of a yellow gel-like distillation residue was 87%, and the distillation yield was 95%. According to $^{13}$C-NMR and GC-MS analyses, the ester dimer was confirmed to be a stereoisomer mixture of 16 kinds composed of eight pairs of racemates.

Spectral Data of 2-n-heptyl-1,3-dioxan-5-one $^1$H-NMR (400 MHz, CDCl$_3$, $\delta_{ppm}$): 0.88 (3H, t, J=6.8 Hz), 1.23-1.37 (8H, m), 1.40-1.47 (2H, m), 1.69-1.74 (2H, m), 4.28 (2H, d, J=18.2 Hz), 4.40 (2H, d, J=18.2 Hz), 4.86 (1H, t, J=5.0 Hz)

$^{13}$C-NMR (100 MHz, CDCl$_3$, $\delta_{ppm}$): 14.0, 22.6, 24.0, 29.1, 29.3, 31.7, 34.0, 72.2, 100.4, 204.5

IR (neat, cm$^{-1}$): 2956, 2858, 1741, 1134, 1053, 957

MS (m/z): 200 (M$^+$), 101, 71, 55, 43

Spectral Data of (2-n-Heptyl-1,3-dioxolan-4-yl) methyl 2-n-heptyl-1,3-dioxolane-4-caboxylate (Stereoisomer Mixture)

IR (neat, cm$^{-1}$): 2925, 2854, 1747, 1458, 1198, 1147, 949

MS (m/z, common to eight peaks on GC): 400 (M$^+$), 301, 173, 157, 101, 69, 57, 43

Spectral Data of 4-Formyl-n-heptyl-1,3-dioxolane (Stereoisomer Mixture)

MS (m/z, common to two peaks on GC): 200 (M$^+$), 171, 101, 69, 55, 41

FIG. 4 is a GC chart of the reaction solution obtained in Example 2-4.

Example 2-5: Production of Ethyl Glycerate

The reaction which was performed in Production Example 2-5 is as follows.

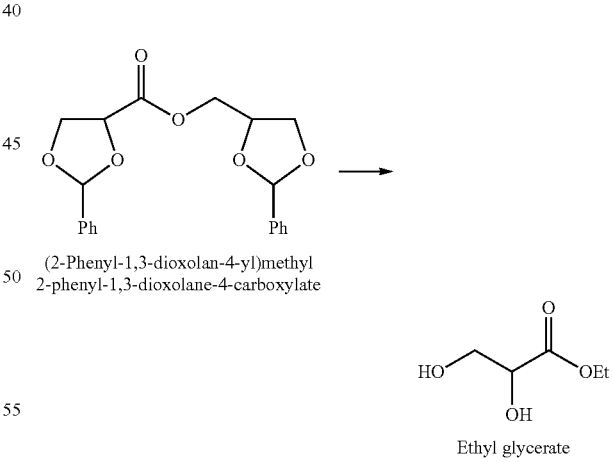

(2-Phenyl-1,3-dioxolan-4-yl)methyl 2-phenyl-1,3-dioxolane-4-carboxylate

Ethyl glycerate

In a 30-mL flask, 2.00 g of (2-phenyl-1,3-dioxolan-4-yl) methyl 2-phenyl-1,3-dioxolane-4-carboxylate (purity: 90.6%, 5.08 mmol) obtained in Examples 2-2-1 and 2-2-2, 100 mg of methanesulfonic acid (purity: 98.0%, 1.02 mmol), and 10.0 g of ethanol (purity: 99.5%, 216 mmol) were charged and refluxed for 3 hours. After cooling, the resultant was neutralized with a 1 mol/L sodium hydroxide solution, and the ethanol was distilled off. To the residue, 20 mL of ion exchanged water was added, and the resultant was extracted twice with 50 mL of tert-butylmethyl ether to remove a water-insoluble product, followed by distilling off the water. Subsequently, 827 mg of the resulting dark orange-colored oily crude product was purified with a Kugelrohr distillation apparatus. There was thus obtained 548 mg of ethyl glycerate which was distilled out as a colorless liquid under conditions at 0.13 kPa (absolute pressure) and at an apparatus-set temperature of 150 to 155° C. The purity was 97.0%, and the yield was 78%.

<Spectral Data of Ethyl Glycerate>

$^1$H-NMR (400 MHz, CDCl$_3$, $\delta_{ppm}$): 1.31 (3H, t, J=6.8 Hz), 3.82-3.92 (2H, m), 4.24-4.30 (3H, m); the $^1$H peak of the hydroxy group became broad, so that it could not be detected.

$^{13}$C-NMR (100 MHz, CDCl$_3$, $\delta_{ppm}$): 14.1, 62.0, 64.1, 71.8, 173.0

IR (neat, cm$^{-1}$): 3425 (br), 2974, 2935, 1728, 1201, 1111, 1063, 1020

MS (m/z): 134 (M$^+$), 104, 76, 61, 43, 31

INDUSTRIAL APPLICABILITY

The ester dimer of the present invention (glyceric acid ester in which hydroxy groups at the 2-position and 3-position are protected as a cyclic acetal group) is efficient in the recovery at the time of production and is, for example, useful as synthetic intermediates, such as glyceric acid, a glyceric acid salt, and a deprotected glyceric acid ester, which are used as raw materials, such as various medicaments, cosmetics, detergents, and polymers.

The invention claimed is:

1. A method of producing a compound represented by the following formula (II), comprising a step of oxidatively esterifying a compound represented by the following formula (I):

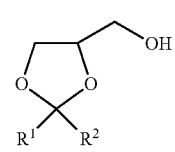
(I)

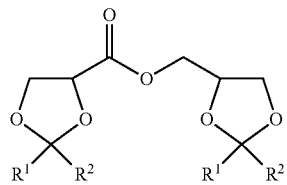
(II)

wherein, in the formulae (I) and (II), R$^1$ and R$^2$ each independently represent a hydrogen atom or a monovalent hydrocarbon group, or R$^1$ and R$^2$ are bonded to each other to form a divalent hydrocarbon group for constituting a ring structure, provided that the case where R$^1$ and R$^2$ are a methyl group at the same time is excluded.

2. The production method according to claim 1, comprising a step of oxidatively esterifying a mixture of a compound represented by the following formula (I) and a compound represented by the following formula (V):

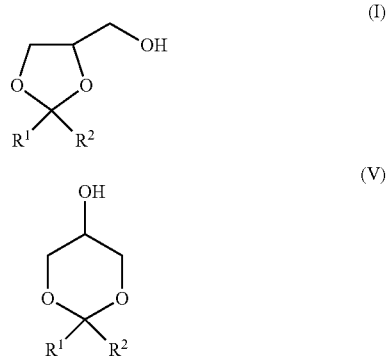

wherein, in the formulae (I) and (V), R$^1$ and R$^2$ each independently represent a hydrogen atom or a monovalent hydrocarbon group, or R$^1$ and R$^2$ are bonded to each other to form a divalent hydrocarbon group for constituting a ring structure, provided that the case where R$^1$ and R$^2$ are a methyl group at the same time is excluded.

3. The production method according to claim 1, wherein in the step of performing oxidative esterification, a compound selected from an organic nitroxyl radical, an N-hydroxy form thereof, and a salt containing an oxo ammonium cation of them, an oxidizing agent, and a base are used.

4. The production method according to claim 3, wherein the base is a heterocyclic aromatic amine having a pyridine skeleton.

5. The production method according to claim 3, wherein the organic nitroxyl radical is a compound represented by the following formula (VIII), a compound represented by the following formula (IX), or a compound represented by the following formula (X):

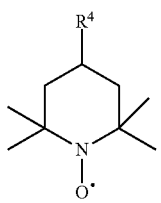
(VIII)

(IX)

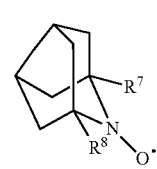
(X)

wherein, in the formula (VIII), $R^4$ represents a hydrogen atom, a halogen atom, a hydroxy group, an alkoxy group, an acyloxy group, an alkoxycarbonyl group, an amino group, an acylamino group, a sulfonyloxy group, an N-alkylcarbamoyloxy group, a carboxy group, a cyano group, an isocyanato group, an isothiocyanato group, or an oxo group; in the formula (IX), $R^5$ and $R^6$ each independently represent a hydrogen atom or a methyl group; and, in the formula (X), $R^7$ and $R^8$ each independently represent a hydrogen atom or a methyl group.

6. The production method according to claim 3, wherein the oxidizing agent is an oxidizing agent composed of a compound containing a halogen.

7. The production method according to claim 1, comprising, after the step of performing oxidative esterification, a step of separating the compound represented by the formula (II).

8. The production method according to claim 7, wherein the separation in the step of separating the compound represented by the formula (II) is separation through distillation.

9. A method of producing glyceric acid, a glyceric acid salt, or a deprotected glyceric acid ester, comprising a step of producing the compound represented by the formula (II) by the production method according to claim 1; and a step of subjecting the compound represented by the formula (II), which is produced in said step, to hydrolysis or alcoholysis.

10. A compound represented by the following formula (II):

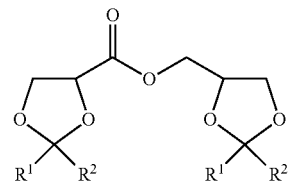

(II)

wherein, in the formula (II), $R^1$ and $R^2$ each independently represent a hydrogen atom or a monovalent hydrocarbon group, or $R^1$ and $R^2$ are bonded to each other to form a divalent hydrocarbon group for constituting a ring structure, provided that the case where $R^1$ and $R^2$ are a methyl group at the same time is excluded.

11. The compound according to claim 10, wherein $R^1$ and $R^2$ are each a monovalent hydrocarbon group having 1 or more and 8 or less carbon atoms.

12. The compound according to claim 10, wherein $R^1$ and $R^2$ are bonded to each other to constitute a cyclopentane ring or a cyclohexane ring.

13. The compound according to claim 10, wherein $R^1$ is a methyl group, and $R^2$ is an ethyl group.

14. The compound according to claim 10, wherein $R^1$ is a hydrogen atom or a monovalent hydrocarbon group having 1 or more and 20 or less carbon atoms, and $R^2$ is a hydrogen atom.

15. The compound according to claim 10, wherein $R^1$ is a hydrogen atom, a methyl group, or a phenyl group, and $R^2$ is a hydrogen atom.

* * * * *